US008217010B2

(12) United States Patent
Gulati

(10) Patent No.: US 8,217,010 B2
(45) Date of Patent: *Jul. 10, 2012

(54) METHODS, COMPOSITIONS AND ARTICLES OF MANUFACTURE FOR CONTRIBUTING TO THE TREATMENT OF SOLID TUMORS

(75) Inventor: Anil Gulati, Naperville, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 69 days.

This patent is subject to a terminal disclaimer.

(21) Appl. No.: 11/360,236

(22) Filed: Feb. 22, 2006

(65) Prior Publication Data

US 2006/0211617 A1  Sep. 21, 2006

Related U.S. Application Data

(63) Continuation-in-part of application No. 10/691,915, filed on Oct. 23, 2003, now abandoned.

(60) Provisional application No. 60/420,960, filed on Oct. 24, 2002, provisional application No. 60/655,656, filed on Feb. 22, 2005, provisional application No. 60/655,654, filed on Feb. 22, 2005, provisional application No. 60/655,643, filed on Feb. 22, 2005.

(51) Int. Cl.
*A61P 35/00* (2006.01)
*A61K 38/00* (2006.01)
*A61K 38/21* (2006.01)
*A61K 33/24* (2006.01)
*A61K 38/04* (2006.01)

(52) U.S. Cl. ...... 514/19.4; 514/1.1; 514/21.5; 424/85.2; 424/85.4; 424/85.5; 424/649

(58) Field of Classification Search .................. 514/2
See application file for complete search history.

(56) References Cited

U.S. PATENT DOCUMENTS

| 5,550,110 A | 8/1996 | Cody et al. |
| 5,612,359 A | 3/1997 | Murugesan |
| 5,811,416 A | 9/1998 | Chwalisz et al. |
| 2002/0082285 A1 | 6/2002 | Lebwohl |
| 2003/0104976 A1 | 6/2003 | Davar et al. |

FOREIGN PATENT DOCUMENTS

| EP | 0655463 A1 | 5/1995 |
| EP | 0815870 A2 | 1/1998 |
| EP | 0950418 A2 | 10/1999 |
| WO | 96/19233 | 6/1996 |
| WO | 00/67024 | 11/2000 |
| WO | 01/00198 | 1/2001 |
| WO | WO 0100198 A2 * | 1/2001 |
| WO | 01/91736 | 12/2001 |
| WO | 03/009805 | 2/2003 |
| WO | 03/045434 | 6/2003 |

OTHER PUBLICATIONS

Filep et al. (Br. J. Pharmacol. 1996; 118 (4): 893-900).*
Rowinsky et al. (N. Engl. J. Med. 1995; 332: 1004-1014).*
Bell et al. (Int. J. Cancer 1999; 80: 295-302).*
Katrina M. Bell, et al., "Effect of Endothelin-1 and Sarafotoxin S6c on Blood Flow in a Rat Tumor", Journal of Cardiovascular Pharmacology, copyright 1995, pp. S222-S225, vol. 26 (Suppl.3).
Aarati Rai and Anil Gulati, "Evidence for the involvement of ETb receptors in ET-1 induced changes in blood flow to the rat breast tumor", Cancer Chemother Pharmacol, copyright Nov. 8, 2002, pp. 21-28, vol. 51.
Takita H., "Effect of vasodilators in experimental solid tumor chemotherapy", Journal of Experimental and Clinical Cancer Research 1983 Italy, copyright 1999, pp. 47-48, vol. 2, No. 1 (Database Embase (online) Elsevier Science Publishers, Amsterdam).
Bruno Battistini and Renia Botting, "Endothelins: A Quantum Leap Forward", Drug News & Perspectives, Aug. 1995, pp. 365-391, vol. 8, No. 6.
Anthony P. Davenport and Bruno Battistini, "Classification of endothelin receptors and antagonists in clinical development", copyright 2002, pp. 1S-3S, vol. 103, No. 48.
N.V.Rajeshkumar, et al., "ET-1(8-21) Increases Blood Perfusion and Enhances Paclitaxel Delivery to the Tumor", Proceeding of the Annual meeting of the American Association for Cancer Research, New York, NY, US, copyright 2005, p. 1349, vol. 96.
Aarati Rai, et al., "ETb receptor agonist, IRL 1620, does not affect paclitaxel plasma pharmacokinetics in breast tumor bearing rats", Journal of Pharmacy and Pharmacology, copyright 2005, pp. 869-879, vol. 57, No. 7.
N.V. Rajeshkumar, et al., "Endothelin B receptor agoinst, IRL 1620, enhances the anti-tumor efficacy of paclitaxel in breast tumor rats", Breast Cancer Research and Treatment,copyright 2005, pp. 237-247, vol. 94, No. 3.
University of Illinois at Chicago: "List of Posters Presentations in 2004 AAPS Annual Meeting (Baltimore)", www2.uic.edu/stud_orgs/prof/aaps/posters.htm, Online pp. 1-4.
Eric K. Rowinsky, M.D.,et al., "Paclitaxel (Taxol)", Review Article The New England Journal of Medicine, Apr. 13, 1995, pp. 1004-1014, vol. 332.
David J. Chaplin, et al., "Modification of Tumor Blood Flow: Current Status and Future Directions", Seminars in Radiation Oncology, Jul. 1998, pp. 151-163, vol. 8, No. 3.
Katrina M. Bell, et al., "Tumor blood flow modification by endothelin-related peptides in the rat HSN fibrosarcoma", British Journal of Cancer, copyright 1996, pp. S161-S163, Supp.27.
Katrina M. Bell, et al., "Vascular Response of Tumor and Normal Tissues to Endothelin-1 following Antagonism of ETa and ETb Receptors in Anaesthetised Rats", copyright 1997, pp. 283-289, vol. 73, No. 2.
Katrina M. Bell, et al., Modification of Blood Flow in the HSN Tumor and Normal Tissues of the Rat by the Endothelin ETb Receptor Agonist, IRL 1620, copyright 1999, pp. 295-302, vol. 80, No. 2.
Kanako Kikuchi, et al.,"Decreased ETb Receptor Expression in Human Metastatic Melanoma Cells", Biphysical Research Communications, copyright 1996, pp. 734-739, vol. 219, No. 3.
Ronit Lahav, et al., "An endothelin receptor B antagonist inhibits growth and induces cell death in human melanoma cells in vitro and in vivo", Proceedings of the National academy of Sciences of USA, copyright Sep. 1999 pp. 11496-11500, vol. 96.

(Continued)

*Primary Examiner* — Karen Canella
(74) *Attorney, Agent, or Firm* — K&L Gates LLP; Louis C. Cullman; Dean G. Stathakis

(57) ABSTRACT

Methods, compositions and articles of manufacture for contributing to the treatment of a solid cancerous tumor are disclosed. The methods, compositions and articles of manufacture can utilize an endothelin B agonist ($ET_B$) to enhance the delivery of a chemotherapeutic agent to a solid tumor in mammals, including humans.

12 Claims, 10 Drawing Sheets

OTHER PUBLICATIONS

Donatella Del Bufalo, et al., "Endothelin-1 acts as a survival factor in ovarian carcinoma cells", Clinical Science, copyright 2002, pp. 302S-305S, vol. 103, No. 48.

J.M. Kroodsma, et al., "Endothelinen:mogelijk een nieuw farmacologisch aangrijpingspunt bij hart-en vaatziekten, nierziekten en oncologische aandoeningen", Nederlands Tijdschrift Voor Geneeskunde, copyright 1997, pp. 1806-1810, vol. 141, No. 38.

Kazuhiko Matsumaru, et al., "Bosentan, a novel synthetic mixed-type endothelin receptor antagonist, attenuates acute gastric mucosal lesions induced by indomethacin and HCI in the rat: Role of endogenous endothelin-1", Journal of Gastroenterology, copyright 1997 pp. 164-170 vol. 32.

A.E. Duggan, et al., "Protection against aspirin-induced human gastric mucosal injury by bosentan, a new endothelin-1 receptor antagonist", Aliment Pharmacol Ther, copyright 1999, pp. 631-635, vol. 13.

Aline S.C. Fabricio, et al., "Essential role for endothelin ETb receptors in fever induced by LPS (*E. coli*) in rats", British Journal of Pharmacology, copyright 1998, pp. 542-548, vol. 125.

Shaifali Bhalla, et al., "Potentiation of morphine analgesia by BQ123, an endothelin antagonist", Peptides, copyright 2002, pp. 1837-1845 vol. 23.

Hemendra N. Bhargava, et al., Modification of Brain and Spinal Cord Dopamine D1 Receptors Labeled with [3H]SCH 23390 After Morphine Withdrawl from Tolerant and Physically Dependent Rats1, The Journal of Pharmacology and Experimental Therapeutics, copyright 1990, pp. 901-907 vol. 252, No. 3.

Michael F. Jarvis, et al., "ABT-627, an endothelin ETa receptor-selective antagonist, attenuates tactile allodynia in a diabetic rat model of neuropathic pain", European Journal of Pharmacology, copyright 2000, pp. 29-35 vol. 388.

Gudarz Davar, et al., "Behavioral signs of acute pain produced by application of endothelin-1 to rat sciatic nerve", NeuroReport, copyright 1998 pp. 2279-2283, vol. 9, No. 10.

Takai, Michihiro, "A Potent and Specific Agonist, Suc-[Glu9, Ala11,15]- Endothelin-1(8-21), IRL 1620, For the ETB Receptor", Biochemical and Biophysical Research Communications, vol. 184, No. 2, 1992, pp. 953-959.

McQueen et al, Endothelin-1 activates ETA receptors to cause reflex scratching in BALB/c mice, Research Paper, Journal, 2007, British Journal of Pharmacology 151, pp. 278-284, Nature Publishing Group.

Davenport, International Union of Pharmacology. XXIX. Update on Endothelin Receptor Nomenclature, Journal, Pharmacological Reviews, vol. 54, No. 2, 2002, pp. 219-226, The American Society for Pharmacology and Experimental Therapeutics.

Paclitaxel (TAXOL) insert, Revised Jan. 2008, Bristol-Meyers Squibb Company.

Ishibashi et al. "Growth of Hepatocarcinoma and Endothelian," Annual Research Report, Foundation for Growth Science, Jul. 1996, No. 19, p. 193-204.

Nelson et al. "Endothelian-1 Production and Decreased Endothelian B Receptor Expression in Advanced Prostate Cancer," Cancer Research, Feb. 15, 1996, vol. 56, No. 4, p. 663-668.

\* cited by examiner

METHODS, COMPOSITIONS AND ARTICLES OF MANUFACTURE FOR CONTRIBUTING TO THE TREATMENT OF SOLID TUMORS

CROSS-REFERENCE TO RELATED APPLICATION

This application is a continuation-in-part of U.S. patent application Ser. No. 10/691,915 filed Oct. 23, 2003 which claims the benefit of U.S. provisional patent application No. 60/420,960, filed Oct. 24, 2002, U.S. provisional patent application No. 60/655,656, U.S. provisional patent application No. 60/655,654, and U.S. provisional patent application No. 60/655,643 all three filed on Feb. 22, 2005, the entire disclosure of which is incorporated herein by reference.

FIELD OF THE INVENTION

The present invention relates to methods, compositions and articles of manufacture for contributing to the treatment of solid tumors, such as breast tumors, in a mammal, through administration of an endothelin agonist and a chemotherapeutic agent.

BACKGROUND OF THE INVENTION

Breast cancer incidence has increased substantially in the last 10 years, and is the single leading cause of death for women ages 40-49 years in the United States. Successful treatment of solid tumors, including breast cancers, remains an unfulfilled medical goal, despite increased understanding of the molecular biology of tumor cells and the availability of an increased number of potential therapeutic agents.

One problem in the treatment of cancers is that an effective dose of a wide variety of potential chemotherapeutic agents is restricted by these agents' non-selective, highly toxic effect on normal tissues. As a result, many patients suffer from the side effects of chemotherapy without reaping the benefits of the treatment. For example, the chemotherapeutic agent paclitaxel inhibits cellular proliferation and induces apoptosis of tumor cells. The clinical utility of paclitaxel has been hampered, however, by its dose limiting toxicities including hypersensitivity, neutropenia and peripheral neuropathy. Thus, there is necessity to develop more specific and less toxic cancer therapies.

Targeted delivery of chemotherapeutic agents to tumors could have the advantage of enhancing the benefit of chemotherapeutic agents while minimizing their systemic toxic effects. Such targeted delivery could also serve to lower the required dose of chemotherapeutic agents thus potentially reducing the unacceptable adverse effects of these agents. One possible way to achieve targeted delivery of chemotherapeutic agents is to utilize the distinctive features of tumor vasculature.

Tumors greater than a few millimeters in size require a constant nutrient supply, and, therefore, develop their own vascular bed and blood flow. Folkman, Cancer Res., 46:467 (1986). Without constant nourishment from these developing blood vessels, the tumors become hypoxic and subsequently die. Recruitment of new vasculature from preexisting blood vessels is termed "angiogenesis."

During angiogenesis, tumor blood vessels develop substantially differently from normal vasculature, and have different properties. Single layered epithelial cells are the first hastily formed tumor blood vessels. These newly formed tumor blood vessels do not have a smooth muscle layer or innervation. Tumors also incorporate mature blood vessels that possess all their autoregulatory functions. Mattsson et al., Tumor Blood Circulation, CRC Press, Boca Raton, pg. 129 (1979); Reinhold, Tumor Blood Circulation, CRC Press, Boca Raton, pg. 115 (1979); Warren, Tumor Blood Circulation, CRC Press, Boca Raton, pg. 26 (1979).

Vascular tone (the degree to which blood vessels are dilated or constricted) is governed by a host of endogenous factors including $H^+$, $K^+$, $Ca^{2+}$, $pO_2$, $pCO_2$ and nitric oxide (NO), as well as other regulatory substances such as endothelin (ET-1). Secombe et al., Landes, Austin, pg. 40 (1994); Luscher et al., The endothelium: modulator of cardiovascular function, CRC Press, Boca Raton, pg. 61 (1990). ET-1 contributes significantly to regulating vascular tone (Yanagisawa et al., Nature, 332:411 (1988)) and investigators have shown an increase in ET1 and $ET_B$ receptor expression in solid tumors including breast carcinomas. Alanen et al., Histopathology, 36:161 (2000); Nelson et al., Cancer Res, 56:663 (1996); Kar et al., Biochem Biophys Res Commun 216:514 (1995); Pagotto et al., J Clin Invest, 96:2017 (1995); Yamashita et al., Cancer Res, 52:4046 (1992); Yamashita et al., Res Commun Chem Pathol Pharmacol, 74:363 (1991). Further, stimulation of $ET_B$ receptors causes an increase in blood supply to tumors through vasodilation of tumor blood vessels. The present invention takes advantage of this fact by using $ET_B$ receptor agonists to selectively increase blood flow to tumors to enhance the targeted delivery of chemotherapeutic agents.

SUMMARY OF THE INVENTION

The present invention is directed to the administration of endothelin agonists and a chemotherapeutic agent to an individual in need thereof to contribute to the treatment of a solid tumor. In particular, tumors have distinctive vasculature including an increased number of $ET_B$ receptors which, when bound, cause vasodilation. Because $ET_B$ receptors are vasodilators, an $ET_B$ receptor agonist, in combination with a chemotherapeutic agent, is useful in the treatment of a solid tumor, such as those found in breast cancers. The $ET_B$ receptor agonist can more effectively deliver chemotherapeutic agents to tumors resulting in enhanced treatment.

Specifically, one embodiment of the present invention includes a method of contributing to the treatment of a solid tumor comprising intravenously administering to a mammal in need thereof an $ET_B$ agonist and a chemotherapeutic agent, wherein the $ET_B$ agonist selectively increases blood supply to the solid tumor thus increasing the delivery of the chemotherapeutic agent to the solid tumor.

In another embodiment of the methods of the present invention, the pharmacokinetics of the chemotherapeutic agent are not affected by the $ET_B$ receptor agonist.

In another embodiment of the methods of the present invention, the $ET_B$ receptor agonist enhances the efficacy of the chemotherapeutic agent.

In another embodiment of the methods of the present invention, the $ET_B$ agonist is selected from the group consisting of ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and mixtures thereof. In another embodiment of the methods of the present invention, the $ET_B$ agonist is IRL1620.

In another embodiment of the methods of the present invention, the chemotherapeutic agent is selected from the group consisting of adriamycin, camptothecin, carboplatin, cisplatin, daunorubicin, doxorubicin, alpha interferon, beta interferon, gamma interferon, interleukin 2, irinotecan, docetaxel, paclitaxel, topotecan, and mixtures thereof. In another embodiment of the methods of the present invention, the chemotherapeutic agent is paclitaxel.

In another embodiment of the methods of the present invention, the solid tumor is selected from the group consisting of an ovarian tumor, a colon tumor, Kaposi's sarcoma, a breast tumor, a melanoma, a prostate tumor, a meningioma, a liver tumor, and a breast phyllode tumor. In another embodiment of the methods of the present invention, the solid tumor is a breast tumor.

In another embodiment of the methods of the present invention, the $ET_B$ agonist and the chemotherapeutic agent are administered according to a strategy selected from the group consisting of administering the $ET_B$ agonist and the chemotherapeutic agent as a single composition; administering the $ET_B$ agonist and the chemotherapeutic agent as separate compositions; administering the $ET_B$ agonist and the chemotherapeutic agent sequentially with the $ET_B$ agonist administered before the chemotherapeutic agent; and administering the $ET_B$ agonist and the chemotherapeutic agent sequentially with the chemotherapeutic agent administered before the $ET_B$ agonist.

In another embodiment of the methods of the present invention, the mammal is a human.

The present invention also includes articles of manufacture. In one embodiment, the article of manufacture comprises (a) a packaged composition comprising an $ET_B$ agonist, and; (b) an insert providing instructions for the intravenous administration of the $ET_B$ agonist to contribute to the treatment of a solid tumor in a mammal; and (c) a container for the (a) $ET_B$ agonist and (b) the insert.

In another embodiment of the articles of manufacture of the present invention, the article of manufacture further comprises (d) a chemotherapeutic agent, and the instructions provide for the administration of the $ET_B$ agonist and the chemotherapeutic agent and the container (c) is for (a) the $ET_B$ agonist, (b) the insert, and (d) the chemotherapeutic agent.

In another embodiment of the articles of manufacture of the present invention, when the instructions are followed, the $ET_B$ agonist selectively increases blood supply to the solid tumor thus increasing the delivery of the chemotherapeutic agent to the solid tumor.

In another embodiment of the articles of manufacture of the present invention, the pharmacokinetics of the chemotherapeutic agent are not affected by the $ET_B$ receptor agonist.

In another embodiment of the articles of manufacture of the present invention, the $ET_B$ receptor agonist enhances the efficacy of the chemotherapeutic agent.

In another embodiment of the articles of manufacture of the present invention, the $ET_B$ agonist is selected from the group consisting of ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$] ET-1, and mixtures thereof. In another embodiment of the articles of manufacture of the present invention, the $ET_B$ agonist is IRL1620.

In another embodiment of the articles of manufacture of the present invention, the chemotherapeutic agent is selected from the group consisting of adriamycin, camptothecin, carboplatin, cisplatin, daunorubicin, doxorubicin, alpha interferon, beta interferon, gamma interferon, interleukin 2, irinotecan, docetaxel, paclitaxel, topotecan, and mixtures thereof. In another embodiment of the articles of manufacture of the present invention, the chemotherapeutic agent is paclitaxel.

DETAILED DESCRIPTION

I. Definitions

Figure 1:
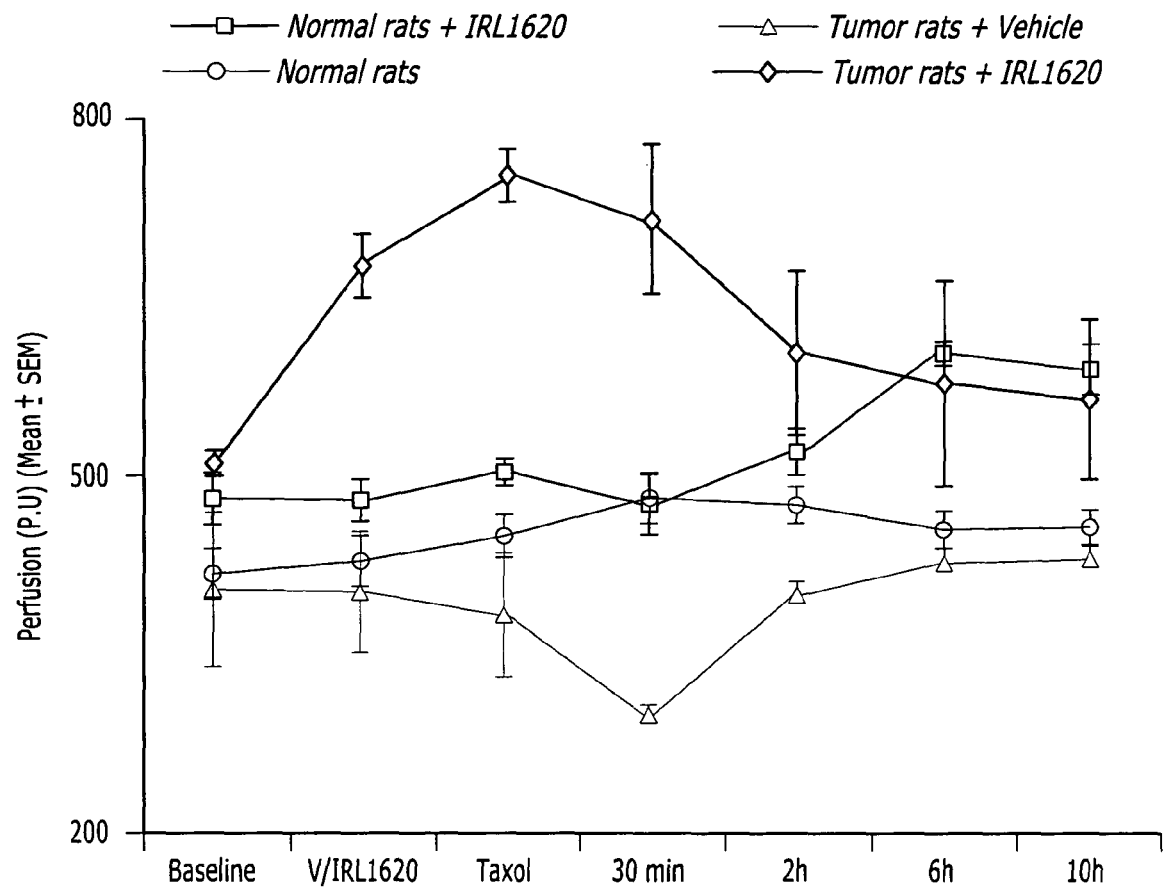
FIG. 1 shows the effect of IRL1620 on paclitaxel-induced changes in tumor perfusion.
Figure 2A:
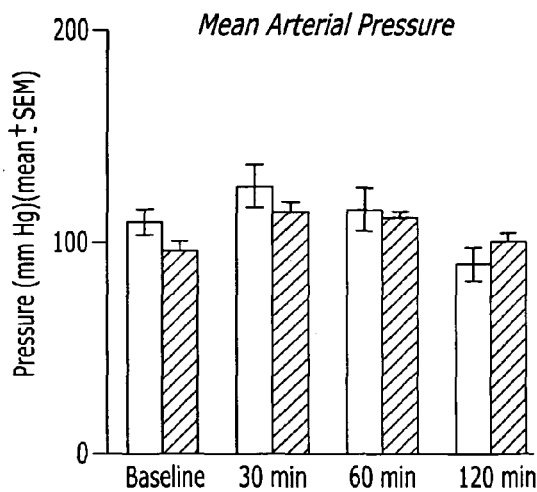
FIGS. 2A-2E show the effect of ET-1 on systemic hemodynamics of cancer-free and breast tumor-bearing rats.
Figure 2B:
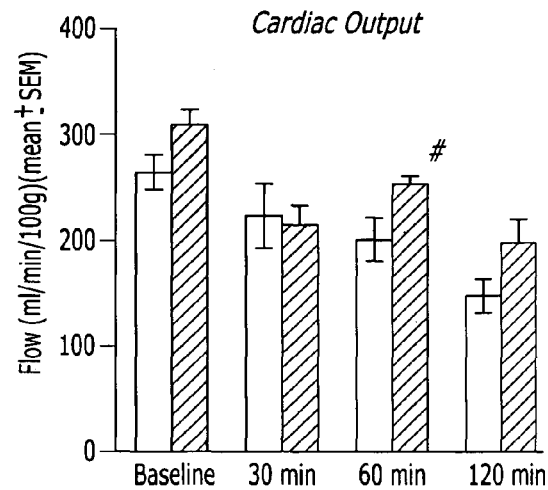
Figure 2C:
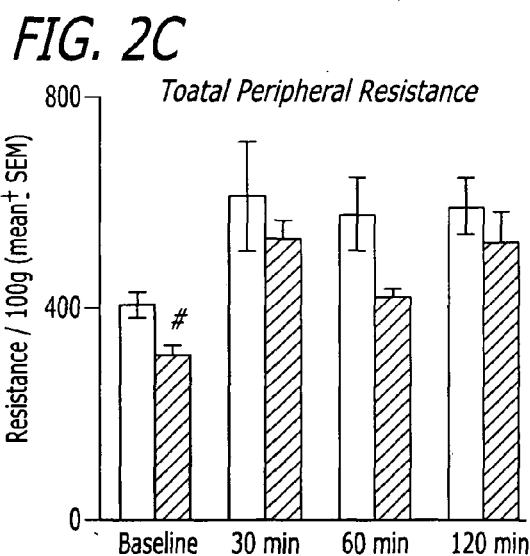
Figure 2D:
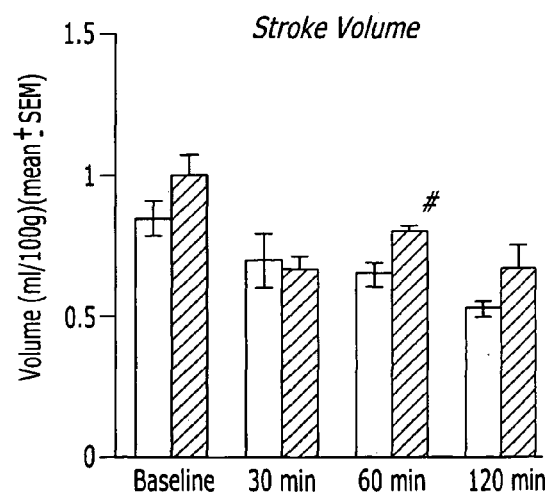
Figure 2E:
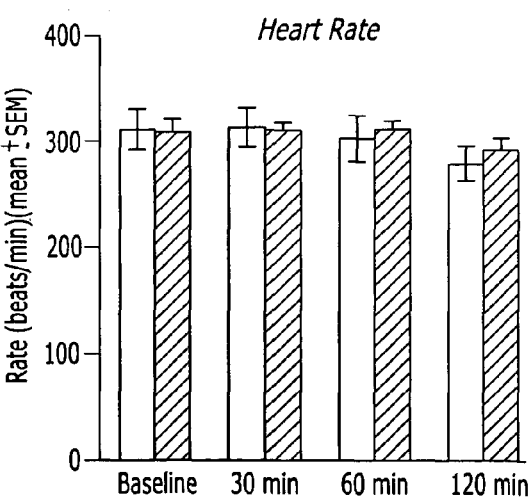

Some terms that are used herein are described as follows:

The terms "treatment" or "contributing to the treatment of" include preventing, retarding the progression or growth of, shrinking, or eliminating a solid tumor. As such, these terms include both medical therapeutic and/or prophylactic administration, as appropriate.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product. An insert can come in many forms including, without limitation, a paper insert or a c.d. rom.

The term "prodrug" means compounds that transform rapidly in vivo to a compound useful in the invention, for example, by hydrolysis. A thorough discussion of prodrugs is provided in Higuchi et al., Prodrugs as Novel Delivery Systems, Vol. 14, of the A.C.S.D. Symposium Series, and in Roche (ed.), Bioreversible Carriers in Drug Design, American Pharmaceutical Association and Pergamon Press, 1987.

Most chemotherapeutic agents have cytotoxic properties that are targeted to destroy cancer cells, but in the process inflict considerable damage to the body's normal physiological systems. It would be of great advantage, therefore, to selectively deliver chemotherapeutic agents to solid tumors thus helping to avoid these negative effects of cancer treatment.

The angioarchitecture of tumor blood vessels is different from that of normal blood vessels. Carmeliet & Jain, Nature, 407:249 (2000). Therefore, the vascular reactivity of tumors differs from that of normal tissue. For example, the administration of nitric oxide donors, nicotinamide and bradykinin agonists modulate blood flow to tumors. Jordan et al., Int J Radiat Oncol Biol Phys, 48:565 (2000); Fukumura et al., Am J Pathol, 150:713 (1997); Hirst et al., Br J Radiol, 67: 795 (1994).

Endothelin is a vasoactive substance that modulates blood flow and is present in large concentrations in breast carcinoma tissues compared to normal breast tissue (specifically, endothelin can be present in an amount of about 12 pg/mg in breast carcinoma tissues as compared to about 0.12 pg/mg in normal breast tissue). Kojima et al., Surg Oncol, 4(6):309 (1995); Kurbel et al., Med Hypotheses, 52(4):329 (1999); Patel et al., Mol Cell Endocrinol, 126(2):143 (1997); Yamashita et al., Cancer Res, 52(14):4046 (1992); Yamashita et al., Res Commun Chem Pathol Pharmacol, 74(3):363 (1991). Endothelins are a family of cyclic peptides with 21 amino acids, comprising three isoforms in mammals, ET-1, ET-2 and ET-3. Inoue et al., Proc Natl Acad Sci USA 86:2863 (1989); Yanagisawa et al., Nature, 332:411 (1988). Endothelins exert their effects by binding to two distinct cell surface receptors, $ET_A$ and $ET_B$. The $ET_B$ receptor binds the three peptide isotypes with equal affinity. In contrast, the $ET_A$ receptor binds ET-1 with higher affinity than the other isoforms. Both receptors belong to the G protein-coupled receptor system and mediate biological responses from a variety of stimuli, including growth factors, vasoactive polypeptides, neurotransmitters and hormones. Masaki, J Cardiovasc Pharmacol, 35:S3 (2000); Gulati, Preface. Adv Drug Deliv Rev, 40:129 (2000); Gulati et al., Am J Physiol, 273:H827 (1997); Levin, N Engl J Med, 333:356 (1995). ETB receptors, a focus of the present invention, are present on both endothelial cells (ECs) and vascular smooth muscle cells (VSMCs) and are increased in breast cancer tissue (including in invasive as well as in ductal and lobular breast carcinoma tissue in humans) when compared to normal breast tissue. Wulfing et al., Oncol Rep, 11:791 (2004); Wulfing et al., Clin Cancer Res, 9:4125 (2003); Alanen et al., Histopathology, 36(2):161 (2000). Endothelin acts on $ET_B$ receptors to produce vascular dilation and increase blood flow to breast tumor tissue. $ET_B$ receptors predominating on ECs, produce vasodilatation via the release of factors such as prostacyclin and nitric oxide. de Nucci et al., Proc Natl Acad Sci USA, 85:9797 (1988). Because ET-1 produces an increase in blood flow to tumors by stimulating $ET_B$ receptors, an $ET_B$ receptor agonist can be used to selectively increase blood supply to tumors, thus increasing the targeted delivery and resulting efficacy of chemotherapeutic agents.

$ET_B$ receptors have been shown in, for example and without limitation, ovarian cancers, myofibroblasts, Kaposi's sarcoma tumor and intratumoral vessels, breast cancers and melanomas. Bagnato et al., Am J Pathol, 158:841 (2001); Alanen et al., Histopathology, 36(2):161 (2000); Bagnato et al., Cancer Res, 59:720 (1999); Kikuchi et al., Biochem Biophys Res Comm, 219:734 (1996). Therefore, administration of an $ET_B$ receptor agonist in combination with a chemotherapeutic agent can be used to contribute to the treatment of solid tumors, including, without limitation, ovarian cancer, colon carcinoma, Kapoli's sarcoma, breast cancer, and melanomas.

$ET_B$ agonists useful in accordance with the present invention include, without limitation, ET-1, ET-2, ET-3, BQ3020, IRL1620 (N-suc-[Glu$^9$, Ala$^{11,15}$]ET-1 (8-21)), sarafotoxin 56c, [Ala$^{1,3,11,15}$]ET-1, and mixtures thereof. [Ala$^{1,3,11,15}$]ET-1 is a linear analog of ET-1 in which the disulfide bridges have been removed by substitution of Ala for Cys residues. Saeki et al., Biochem Biophys Res Commun, 179:286 (1991). BQ3020 and IRL1620 are truncated linear synthetic analogs of ET-1 and are the most widely used selective synthetic agonists. IRL1620 is a linear ET-analog whose structure is based on the carboxy terminal end of ET-1 and has 120,000 fold selectivity for the $ET_B$ receptors. Okada & Nishikibe, Cardiovasc Drug Rev, 20:53 (2002); Douglas et al., Br J Pharmacol, 114:1529 (1995). IRL1620 is a highly selective and potent $ET_B$ agonist, with evidence being reported of its selectivity for the $ET_{B1}$ receptor subtype in preference over the $ET_{B2}$ subtype. Brooks et al., J Cardiovasc Pharmacol, 26 Suppl 3:S322 (1995).

Chemotherapeutic agents useful in accordance with the present invention include, for example and without limitation, alkylating agents, antimetabolites, hormones and antagonists thereof, radioisotopes, antibodies, as well as natural products, and mixtures thereof. For example, an $ET_B$ agonist can be administered with antibiotics, such as doxorubicin and other anthracycline analogs, nitrogen mustards, such as, without limitation, cyclophosphamide, pyrimidine analogs such as, without limitation, 5-fluorouracil, cisplatin, hydroxyurea, and its natural and synthetic derivatives, and the like. As another example, in the case of mixed tumors, such as adenocarcinoma of the breast, where the tumors include gonadotropin-dependent and gonadotropin-independent cells, the $ET_B$ agonist can be administered in conjunction with, without limitation, leuprolide or goserelin (synthetic peptide analogs of LH-RH). Additional non-limiting examples of chemotherapeutic agents that can be used with the present invention include adriamycin, camptothecin, carboplatin, cisplatin, daunorubicin, doxorubicin, interferon (alpha, beta, and/or gamma), interleukin 2, irinotecan, docetaxel, paclitaxel, topotecan, and therapeutically effective analogs and derivatives of the same.

In one embodiment of the present invention, an endothelin agonist is used in conjunction with a chemotherapeutic agent to contribute to the treatment of a solid tumor. In this method, the endothelin agonist, notably an $ET_B$ agonist, increases blood flow to the tumor, which is rich in $ET_B$ receptors. The $ET_B$ agonist, therefore, provides a more selective target for the chemotherapeutic agent and improves the chemotherapeutic effect of the agent.

It is theorized, but not relied upon herein, that endothelin agonists stimulate $ET_B$ receptors to dilate tumor blood vessels, thereby increasing blood flow and the resultant delivery of chemotherapeutic agents to the tumor. The increased blood perfusion of tumors caused by endothelin agonists also increases oxygenation of the tissue. Improved oxygenation can enhance the therapeutic action of chemotherapeutic agents. Endothelin also can have mitogenic properties. The mitogenic actions of endothelin can help increase the action of chemotherapeutic agents, when administered together. The mitogenic action of an endothelin agonist can increase the action of chemotherapeutic agents by improving their incorporation into dividing cells, thus increasing their efficacy.

Chemotherapy is frequently indicated as an adjuvant to surgery in the treatment of a cancer. The goal of chemotherapy in the adjuvant setting is to reduce the risk of recurrence and enhance disease-free survival when the primary tumor has been controlled. Chemotherapy is utilized as a treatment adjuvant for a cancer, frequently when the disease is metastatic. An $ET_B$ agonist, therefore, is particularly useful before or following surgery in the treatment of a solid tumor in combination with chemotherapy.

EXAMPLE 1

Effect of IRL1620 and Paclitaxel on Breast Tumor Perfusion Methods

The following studies were conducted to examine the systemic hemodynamics and regional circuitry effects of ET-1 in normal and breast tumor-bearing rats.

One extensively studied breast tumor model is the chemically induced rat mammary carcinogenesis model. van Zwieten, The rat as animal model in breast cancer research. Martinus Nijhoff Publishers, Boston, pg. 206 (1984); Dao et al., J Natl Cancer Inst, 71:201 (1983); Russo et al., J Natl Cancer Inst, 61:1439 (1978). Huggins et al., Science, 137 (1962); Huggins et al., Proc Natl Acad Sci USA, 45:1294 (1959). Chemically induced mammary tumorigenesis in rats is the model most closely resembling a human cancer. Russo et al., Lab Invest, 62:244 (1990). In terms of tissue architecture, the mammary gland of a rat is comparable to that of human women. It is formed by an epithelium that covers the ducts and alveoli and a stroma, the connective tissue scaffolding of this organ. These two compartments are in continuous interaction during embryonic development and throughout adulthood. Therefore, this autochthonous experimental model was selected as a model in the presently described studies as it most closely resembles human cancer. Id.

Chemically induced rat mammary carcinogenesis typically is achieved by administration of 7,12-dimethylbenzene(a)anthracene (DMBA) or N-methylnitrosourea (MNU). Rogers et al., Chemically induced mammary gland tumors in rats: modulation by dietary fat. Alan R. Liss, Inc., New York 255 (1996). Tumors induced by DMBA or MNU have different morphological characteristics. In particular, tumors induced by MNU are more localized at the breast and are less likely to metastasize. Macejova et al., Endocr Regul, 35:53 (2001). Therefore, MNU often is chosen as the chemical agent for the specific induction of breast tumors in rats. These breast tumors can be benign with fibroadenomas and papillomas, or they can be malignant. van Zwieten, The rat as animal model in breast cancer research. Martinus Nijhoff Publishers, Boston, pg. 206 (1984). Rats have six pairs of mammary glands, one in the cervical region, two in the thoracic region, one in the abdominal region, and two in the ingual region. Id.; Astwood et al., Am J Anat, 61 (1937). Virgin rats treated with MNU develop more tumors in the thoracic region than the abdominal region. Russo et al., Lab Invest, 57:112 (1987).

Methods

Female Sprague Dawley rats (Harlan Co., Madison, Wis.) weighing 180-200 grams (g) were used. All animals were housed, three to a cage, in a temperature controlled room (23±1° C.), humidity (50±10%), and artificial light (0600-1800 hr). The animals were given food and water ad libitum. The experiments were conducted after the animals had been acclimatized to the environment for at least four days.

N-methylnitrosourea (MNU) was purchased from Ash Stevens Inc. (Detroit, Mich.). IRL1620 and Endothelin-1 (ET-1) were obtained from American Peptide Company Inc. (Sunnyvale, Calif.). ET-1 was dissolved in 0.1% albumin.

MNU (50 mg/kg) or saline (1 ml/kg) was administered intraperitoneally (i.p.) to the female Sprague Dawley rats. After tumors reached 2-4 cm in diameter, blood flow experiments were performed.

Rats were anesthetized with urethane (1.5 g/kg, i.p.) (Sigma Chemicals, St. Louis, Mo.), and the left femoral vein was cannulated (PE 50 tubing, Clay Adams, Parsipanny, N.J.) for drug administration.

Animals were divided into the following groups:
 (i) Saline injection followed by paclitaxel (3 mg/kg) after 15 minutes in normal rats (N=4);
 (ii) IRL1620 (3 nmol/kg) injection followed by paclitaxel (3 mg/kg) after 15 minutes in normal rats (N=4);
 (iii) Saline injection followed by paclitaxel (3 mg/kg) after 15 minutes in tumor bearing rats (N=4); and
 (iv) IRL1620 (3 nmol/kg) injection followed by paclitaxel (3 mg/kg) after 15 minutes in tumor bearing rats (N=4).

Blood perfusion to the mammary gland of the rats was measured using laser Doppler flowmetry. See Song et al., Int J Radiat Oncol Biol Phys, 18:903 (1990); Song et al., Int J Radiat Oncol Biol Phys, 17:1041 (1989). In this procedure, the animals were shaved around the nipples and the skin surrounding the mammary glands was dissected out. A standard model fiber optic probe was secured to the mammary artery and connected to a Periflux PF2b 4000 Laser Doppler Flowmetry (Perimed KB, Stockholm, Sweden). The time constant was set to 1.5 seconds, and the band width was set to 4 KHz. Data were analyzed using analysis of variance (ANOVA) followed by Duncan's test. A level of $p<0.05$ was considered significant.

Results

No change in blood flow to the breast tissue of normal rats was observed following the administration of saline or IRL1620 and paclitaxel. Significant differences were observed between the blood flow in tumor tissue after IRL1620 injection (36.3%, $p<0.05$) and after paclitaxel administration (51.9%, $p<0.0\text{-}5$) from baseline (see FIG. 1).

EXAMPLE 2

Effect of ET-1 Infusion on Systemic Hemodynamics and Blood Flow to the Mammary Tissue of Normal and Tumor-bearing Rats Methods MNU and saline treatments were performed as i.p. injections three months prior to the study. Rats were palpated regularly starting four weeks after the treatments. Once tumors reached 4-8 mm in diameter, the experiments were initiated.

Rats were anesthetized with urethane (1.5 g/kg, i.p.) (Sigma Chemicals, St. Louis, Mo.). All surgical areas were shaved and cleaned with alcohol swabs. The left femoral vein was cannulated (PE 50 tubing, Clay Adams, Parsipanny, N.J.) for drug administration. The left femoral artery was cannulated (PE 50 tubing) and was used for withdrawal of reference blood sample in microsphere studies using a withdrawal pump (Model 22, Harvard Apparatus, South Natick, Mass.). The right femoral artery was cannulated (PE 50 tubing) and connected to a Gould P23 ID pressure transducer for recording the blood pressure on a Grass P7D polygraph (Grass Instrument Co., Quincy, Mass., USA) through a 7PI preamplifier. The heart rate (HR) was recorded through a 7P4B Grass tachograph (Grass Instrument Co., Quincy, Mass.) triggered from blood pressure signals. The right carotid artery was exposed and a PE 50 tubing was guided through the common carotid artery into the left ventricle. The presence of the cannula in the left ventricle was confirmed by recording the pressure on the Grass polygraph using the Statham P23 DC pressure transducer (Grass Instrument Co., Quincy, Mass.). When the cannula reached the left ventricle; the diastolic pressure dropped to zero. In order to maintain the blood $pO_2$, $pCO_2$, and pH constant, and to avoid the effect of respiration on blood pressure and HR, animals were kept on constant rate artificial respiration by inserting an endotracheal cannula connected to a rodent ventilator (Model 683, Harvard Apparatus Inc., South Natick, Mass.).

Rats were initially divided into two groups, each receiving one of the following treatments:
(i) ET-1 (50 ng/kg/min) infusion for 30 minutes in rats treated with saline (N=6); and
(ii) ET-1 (50 ng/kg/min) infusion for 30 minutes in treated with MNU (50 mg/kg, i.p.) (N=6).

The following groups were then studied to evaluate the role of $ET_B$ receptors on the changes induced by ET-1 infusion on the systemic hemodynamics and blood flow to the mammary tissue of normal rats and rats with breast tumors:
(i) BQ788 ((N-cis-2,6-dimethylpiperidinocarbonyl-L-gamma-methyll-eucyl-D-1-methoxycarbonyltrptophanyl-D-Nle); obtained from American Peptide Company Inc. (Sunnyvale, Calif.) and dissolved in saline at 0.5 pmol/kg)) infusion for 20 minutes followed by ET-1 (50 ng/kg/min) infusion for 30 minutes in rats treated with saline (N=5);
(ii) BQ788 (0.5 pmol/kg) infusion for 20 minutes followed by ET-1 (50 ng/kg/min) infusion for 30 minutes in rats treated with MNU (50 mg/kg, i.p.) (N=5).

Systemic hemodynamic and regional circulation parameters were determined at baseline, 30, 60, and 120 minutes after starting ET-1 (50 ng/kg/min) infusion. Because ET-1 infusion was performed for 30 minutes, the 30-minute data shows the effect of ET-1, and the 60- and 120-minute data indicates duration of the ET-1 effect.

Systemic hemodynamics and regional blood circulation were determined using a literature described procedure. See Gulati et al., J Lab Clin Med, 126:559 (1995); Gulati et al., Life Sci., 55:827 (1994); Sharma et al., Artif Cells Blood Substit Immobil Biotechnol, 22:593 (1994). At each measurement, a thoroughly mixed suspension of approximately 100,000 microspheres (15±1 μm diameter) labeled with $^{46}Sc$ (scandium), $^{113}Sn$ (tin), $^{141}Ce$ (cerium), or $^{95}Nb$ (niobium) (New England Nuclear Corporation, Boston, Mass., USA) in 0.2 ml saline were injected into the left ventricle and flushed with 0.3 ml saline over a 15 second period. In order to calculate blood flow, arterial blood was withdrawn at a rate of 0.5 ml/min through the right femoral artery. Blood was withdrawn for 90 seconds starting about 5-10 seconds before microsphere injection. At the end of the experiment, animals were sacrificed with an overdose of pentobarbital sodium. All tissues and organs were dissected out, weighed, and placed in vials. The radioactivity in the standards, the blood samples, and the tissue samples were counted in a Packard Minaxi Auto-Gamma 5000 series gamma counter (Packard Instruments Co., Downers Grove, Ill.) with preset windows discriminating the isotope energies. The following parameters were calculated: (1) cardiac output (CO) ((radioactivity injected×withdrawal rate of arterial blood)/radioactivity in sampled arterial blood), (2) stroke volume (SV) (CO/HR), (3) total peripheral resistance (TPR) (mean arterial pressure (MAP)/CO), (4) regional blood flow ((radioactivity in tissue× withdrawal rate of arterial blood)/radioactivity in sampled arterial blood), and (5) regional vascular resistance (MAP/regional blood flow). The data were calculated using computer programs described in the literature. Saxena et al., Comput Programs Biomed, 12:63 (1980).

Blood perfusion to the mammary gland of the rats was measured using laser Doppler flowmetry. See Song et al., Int J Radiat Oncol Biol Phys, 18:903 (1990); Song et al., Int J Radiat Oncol Biol Phys, 17:1041 (1989). The animals were shaved around the nipples. The skin surrounding the mammary glands was dissected out as a lambeau about 6 cm wide and about 4 cm long. A standard model fiber optic probe was applied to the surface of the lambeau, and secured to the tissue by double stick tape. The lambeau was placed in a metal holder and taped down to prevent movement, then connected to a Periflux PF2b 4000 Laser Doppler Flowmetry (Perimed KB, Stockholm, Sweden). The time constant was set at 1.5 seconds and the bandwidth was set at 4 KHz. Data were analyzed using analysis of variance followed by Duncan's test. A level of $p<0.05$ was considered significant.

Results

The baseline systemic hemodynamic parameters in normal (saline treated) rats were MAP: 111.1±4.8 mmHg; CO:268.6±17.6 ml/min; SV:0.87±0.06 ml; TPR:419.6±24.37 mmHg.min/ml; and HR:312.5±20.2 beats/min. In normal rats, a significant increase in MAP was observed at 30 minutes (14.5%; $p<0.05$), and a decrease at 120 minutes (17.8%; $p<0.05$) following ET-1 infusion. TPR increased at 120 minutes (49.2%; $p<0.05$). CO decreased at 60 and 120 minutes (22.9% and 42.5% respectively; $p<0.05$) after ET-1 infusion. SV decreased at 60 and 120 minutes (20.9% and 36% respectively; $p<0.05$). No significant change in HR was observed (FIGS. 2A-2E).

The baseline systemic hemodynamic parameters in tumor-bearing (MNU treated) rats were similar to that in normal rats. A significant increase in MAP was observed at 30 minutes (19.1%; $p<0.05$) and at 60 minutes (15.3%; $p<0.05$) following ET-1 infusion in tumor-bearing rats. TPR increased at 30 minutes (73.9%; $p<0.05$), 60 minutes (39.7%; $p<0.05$), and 120 minutes (71.4%; $p<0.05$) following administration of ET-1. CO decreased at 30, 60 and 120 minutes (29.4%, 16.7% and 36.1% respectively; $p<0.05$). SV decreased significantly at 30, 60 and 120 minutes (31.1%, 17.9% and 32.1% respectively; $p<0.05$). No change in HR was observed (FIGS. 2A-2E).

Figure 3A:
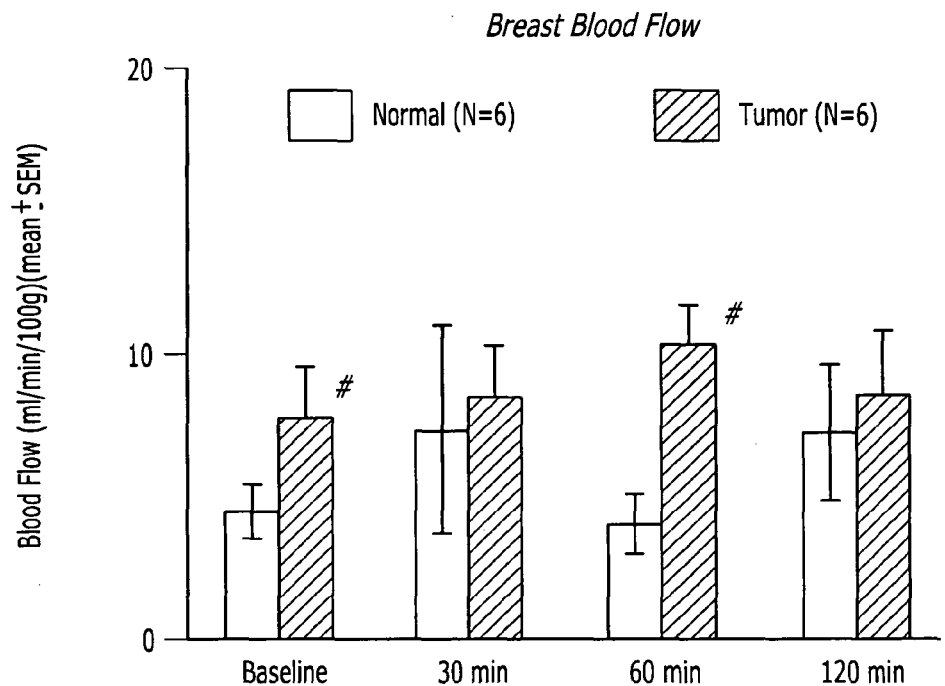
FIGS. 3A-3B show the effect of ET-1 on blood flow and regional vascular resistance in the breast tissue of cancer-free and breast tumor-bearing rats.
Figure 3B:
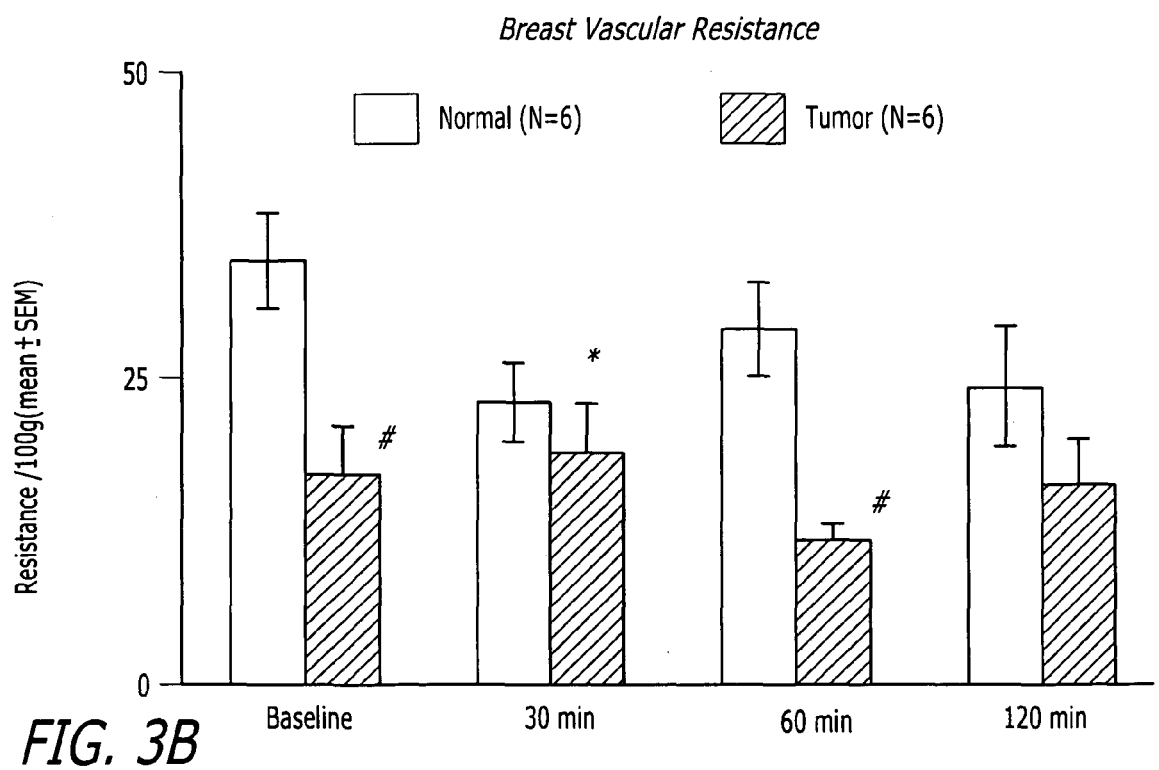

No change in blood flow to the breast tissue of normal saline-treated rats was observed following the administration of ET-1. A significant decrease (18.61%; $p<0.05$) in vascular resistance at 60 minutes was observed, which is 30 minutes post ET-1 infusion, in the breast tissue of normal rats (FIGS. 3A-3B).

Significant differences were observed between the blood-flow and the regional vascular resistance in the breast tissue of tumor-bearing (MNU treated) and normal (saline treated) rats. A significant increase (153%; $p<0.05$) in blood flow to the breast tissue of tumor-bearing rats as compared to normal rats was observed at 60 minutes following administration of ET-1. The vascular resistance in the tumor-bearing rats was significantly different at baseline (102%; $p<0.05$) and at 60 minutes (147%; $p<0,05$) following ET-1 administration compared to normal rats (FIGS. 3A-3B).

Figure 4A:
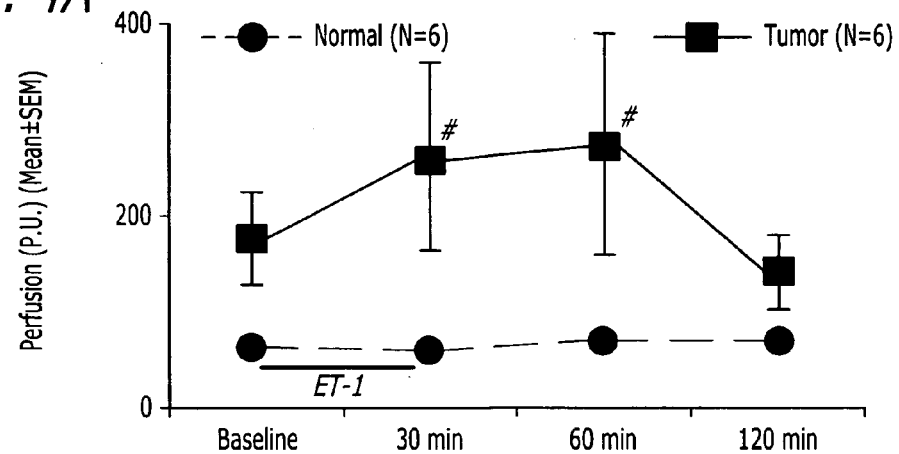
FIGS. 4A-4C show the effect of ET-1 on perfusion, concentration of moving blood cells (CMBC), and velocity of blood cells in breast tissue of cancer-free and breast tumor-bearing rats.
Figure 4B:
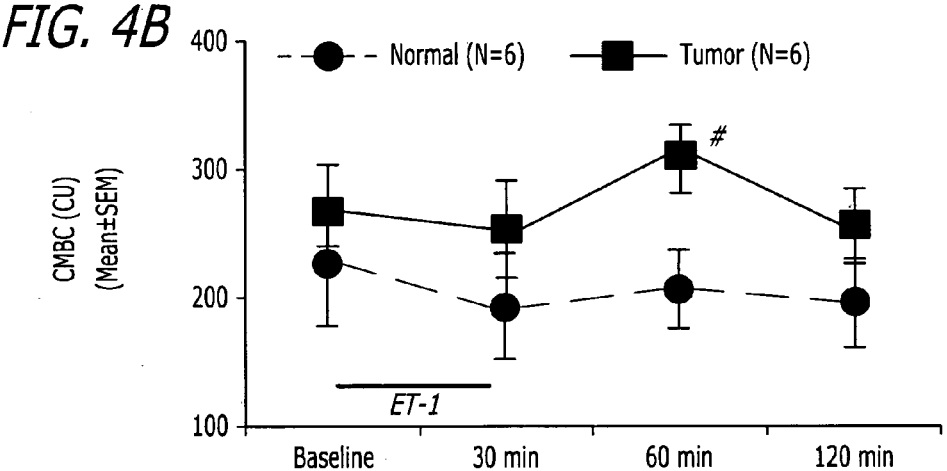
Figure 4C:
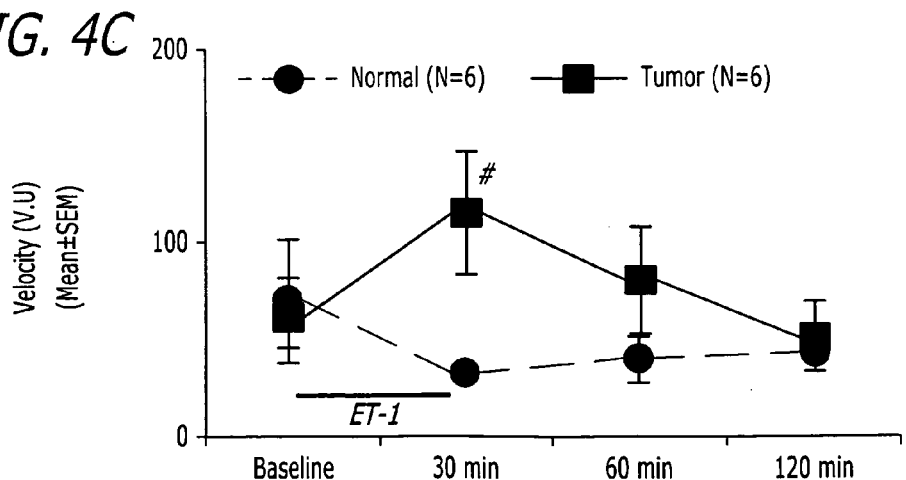

FIGS. 4A-4C show the changes in perfusion, concentration of moving blood cells (CMBC), and velocity of red blood cells (RBC) in the breast tissue of tumor-bearing and normal rats. Blood perfusion in the breast tissue of normal rats did not change after ET-1 administration. Perfusion in the breast tissue of tumor-bearing rats at 30 minutes following ET-1 administration increased significantly (176%; $p<0.05$) compared to normal rats. This increase in perfusion returned to baseline at 60 and 120 minutes following ET-1 administration in tumor-bearing rats.

The CMBC in tumor-bearing rats increased significantly (54%; $p<0.05$) at 60 minutes post ET-1 administration as compared to normal rats. CMBC returned to baseline at 120 minutes after ET-1 administration. The velocity of RBC increased significantly (252%; $p<0.05$) at 30 minutes post ET-1 administration compared to normal rats. Two hours (120 minutes) after ET-1 administration, the velocity of RBC in tumor-bearing rats returned to baseline (FIGS. 4A-4C).

Figure 5A:
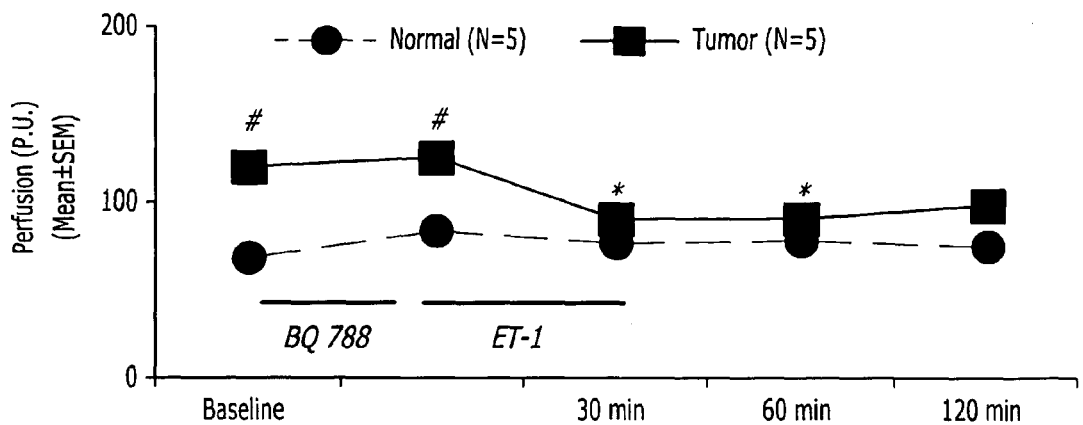
FIGS. 5A-5C show the effect of BQ788 on ET-1-induced changes in blood perfusion, CMBC, and velocity of blood cells in breast tissue of cancer-free and breast tumor-bearing rats.
Figure 5B:
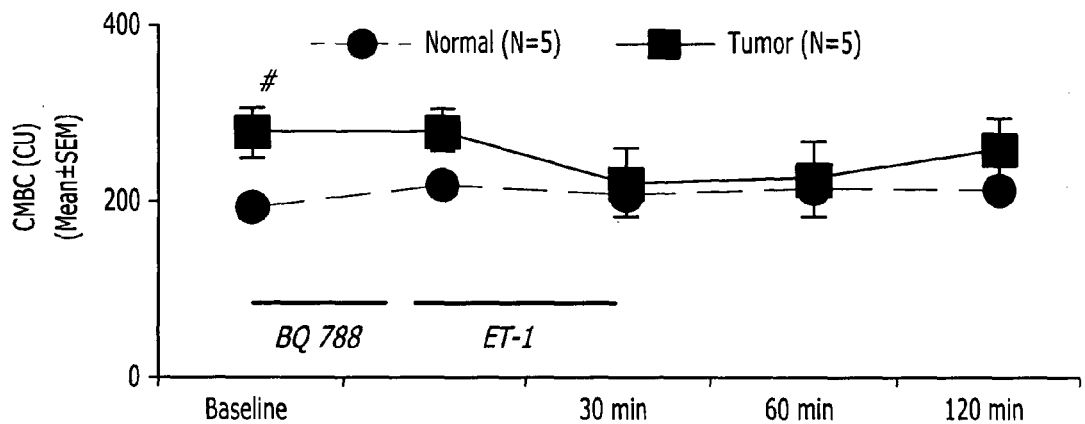
Figure 5C:
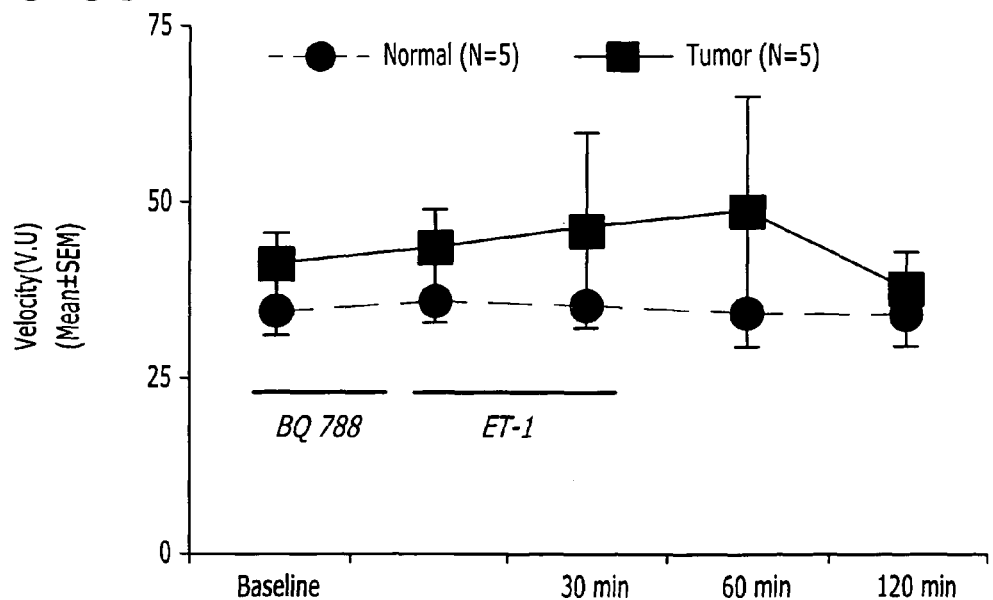

FIGS. 5A-5C show the effect of BQ788 on changes induced by ET-1 in blood perfusion, CMBC, and velocity of RBC in tumor-bearing and normal rats, respectively. Blood perfusion in the breast tissue of normal rats did not change significantly after BQ788 administration or ET-1 infusion. However, perfusion in the breast tumor tissue of tumor-bearing rats decreased significantly at 30 (25.25.+−.5.7%; P<0.05) and 60 minutes (25.17.+−.2.8%; P<0.05) following ET-1 infusion in BQ788 pretreated rats. Pretreatment with BQ788 attenuated the increase in perfusion induced by ET-1 in tumor-bearing rats. No difference between the perfusion in breast tissue of tumor-bearing rats and normal rats was observed following ET-1 administration in BQ788 pretreated rats.

The baseline CMBC in tumor-bearing rats was significantly higher than the baseline CMBC of breast tissue of normal rats (42.4%; P<0.05). However, after BQ788 infusion, no difference between CMBC of tumor-bearing and normal rats was observed. In addition, no difference in velocity of RBC between the two groups was observed (FIGS. 5A-5C).

The above tests show the effect of ET-1 on systemic hemodynamics and blood flow to the breast tissue of saline-treated and MNU-treated tumor-bearing rats. It is known that ET-1 stimulates angiogenesis by promoting production of VEGF. Studies have shown that ET-1 is increased in many cancer tissues like breast carcinoma (Yamashita et al., Res Commun Chem Pathol Pharmacol, 74:363 (1991)), breast phyllode tumor (Yamashita et al., Cancer Res, 52:4046 (1992)), prostate carcinoma (Nelson et al., Cancer Res, 56:663 (1996)), liver carcinoma (Kar et al., Biochem Biophys Res Commun 216:514 (1995)), and some meningiomas (Pagotto et al., J Clin Invest, 96:2017 (1995)). The above tests demonstrate changes in ET-1-induced vascular responses in the breast tumor. The method used in these tests was a well-established radioactive microsphere technique to study the systemic hemodynamics and regional blood circulation. Gulati et al., Am J Physiol, 273:H827 (1997); Gulati et al., Crit Care Med, 24:137 (1996); Gulati et al., J Lab Clin Med, 126:559 (1995); Gulati et al., Life Sci, 55:827 (1994).

Baseline blood flow to the breast tumor tissue of tumor-bearing rats was higher than blood flow in normal animals. This was observed in an earlier study and is theorized, but not relied upon, as being attributed to the recruitment of new blood vessels in the tumor. Vaupel, Blood flow, oxygenation, tissue pH distribution, and bioenergetic status of tumors. Ernst Schering, Research Foundation Lecture 23, Berlin (1994). Blood flow to the breast tumor following ET-1 administration was significantly increased as compared to that observed in the breast tissue of normal rats. Laser Doppler flowmetry showing an increase in blood perfusion to the breast tumor confirmed an increase in blood flow observed in the breast tumor tissue following ET-1 administration. The increase in blood perfusion is theorized, but not relied upon, as being attributed to an increase in either velocity of RBC velocity or CMBC, or both. At the end of ET-1 infusion an increase in velocity of RBC was observed, whereas an increase in CMBC was observed 30 minutes after ET-1 infusion.

Further, the observed increase in blood flow in response to ET-1 is theorized, but not relied upon, as being attributed to $ET_B$ mediated vasodilation. Studies have shown that ET-1 and $ET_B$ receptor expression is augmented in breast cancer tissue. Alanen et al., Histopathology, 36:161 (2000); Yamashita et al., Res Commun Chem Pathol Pharmacol, 74:363 (1991). In accordance with the present invention, it was found that administration of BQ788 blocked the ET-1-induced increase in blood flow to the tumor tissue. BQ788 (i.e., N-cis-2,6-dimethylpiperidinocarbonyl-L-gamma-methyll-eucyl-D-1-methoxycarbonyltrptophanyl-D-Nle) is a specific $ET_B$ receptor antagonist. BQ788 inhibits binding to $ET_B$ receptors with an $IC_{50}$ value of 1.2 nM.

BQ788 was used to determine the role of $ET_B$ receptors in ET-1 induced vasodilation in the breast tumor. This result suggests that ET-1-induced vasodilatory responses are mediated through $ET_B$ receptors. Expression of $ET_B$ receptors is significantly higher in the endothelial cells than in the smooth muscle cells, and is regulated by various growth factors and cytokines. Smith et al., J Cardiovasc Pharmacol, 31:S158 (1998). Normal breast tissue has a higher level of $ET_B$ than $ET_A$ receptors (Alanen et al., Histopathology, 36:161 (2000)), and it is theorized, but not relied upon, that during breast cancer, $ET_B$ receptors are overexpressed and contribute to maintaining blood flow to the tumor tissue.

In summary, the described experiments demonstrate that the infusion of ET-1 produces an increase in blood flow and a decrease in vascular resistance in breast tumor tissue, and that this increase in blood flow can be blocked by an $ET_B$ receptor antagonist.

EXAMPLE 3

Effect of IRL1620 on Tumor Blood Perfusion and Chemotherapeutic Agent Delivery

Previous experiments demonstrated that administration of ET-1 to breast tumor bearing rats increased blood flow selectively to tumor tissue by stimulating $ET_B$ receptors. The experiment described in this example will be conducted to determine the effect of the $ET_B$ receptor agonist, IRL1620 on breast and melanoma tumor perfusion and its effect on paclitaxel accumulation in tumor and other major organs.
Methods Breast tumors will be induced in virgin female Sprague Dawley rats (48 days of age) by N-methyl nitrosourea (MNU; 50 mg/kg, i.p.). Rats with a tumor volume of 300-500 mm³ will be anesthetized with urethane (1.5 g/kg i.p.) and treated with saline (0.3 ml/kg, i.v.) or IRL1620 (3 nmol/kg, i.v) as described previously. Tumor perfusion will be measured for 10 h using a Periflux PF2b 4000 Laser Doppler Flowmetry as described previously. In a second study, nude mice will be subcutaneously inoculated with one million human melanoma cells (UISO-MEL-2). Mice with tumor volume of 300-400 mm³ will be treated with saline or IRL1620 as described previously and perfusion will be measured for 3 h as described previously. Experiments will also be performed to determine whether elevated perfusion increases the accumulation of paclitaxel in tumor tissue. [³H]-paclitaxel (10 µCi/mice) will be administered to melanoma bearing mice 15 min after IRL1620 or saline. Animals will be sacrificed 3 h after [³H]-paclitaxel administration. Tumor and major organs will be excised, weighed and solubilized in tissue solubilizer and radioactivity will be measured through techniques well known to those of ordinary skill in the art. Specifically, the concentrations of [³H]-paclitaxel in the plasma samples will be measured using a Beckman Coulter liquid scintillation counter (model LS 6500). Plasma will be thawed and mixed with 20 mL of liquid scintillation cocktail. The samples will be counted and the counts will be converted from "dpm" units to "fmol/mL" using the following formula:

$$\text{fmol/mL} = \text{dpm value} \times \text{decay factor} \times 2.2 \times 10^{-12}/10^{-12} \times \text{volume of sample in mL}.$$

Results

Figure 6:
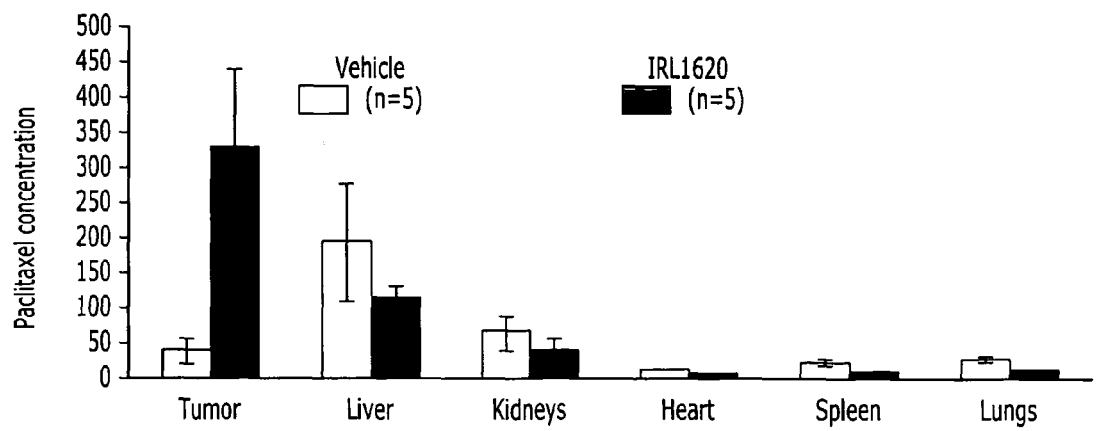
FIG. 6 shows the effect of IRL1620 on paclitaxel accumulation in tumor and other major organs of breast tumor-bearing rats.

IRL1620 will significantly increase tumor perfusion in breast tumor bearing rats and melanoma bearing mice. IRL1620 administration will result in a 150% and 318% increase in tumor perfusion in breast and melanoma bearing animals, respectively. There will be a 730% increase in tumor paclitaxel concentration in mice treated with IRL1620 compared to saline treated mice. However, IRL1620 will not significantly enhance paclitaxel concentration in other major organs. The results will show those depicted in FIG. 6.

EXAMPLE 4

Effect of IRL1620 on Pharmacokinetics of Paclitaxel

Altering blood flow dynamics in the body can significantly affect the pharmacokinetics of a therapeutic moiety, and paclitaxel is known to have complex pharmacokinetic properties. See, for example, Sparreboom et al., Cancer Res 56:2112 (1996a); Gianni et al., J Natl Cancer Inst 87:1169 (1995b); Sonnichsen & Relling, Clin Pharmacokinet 27:256 (1994); Huizing et al., J Clin Oncol 11:2127 (1993); Brown et al., J Clin Oncol 9: 1261 (1991); Longnecker et al., Cancer Treat Rep 71:53 (1987); Wiemik et al., Cancer Res 47:2486 (1987b). It is therefore important to understand the impact of IRL1620 on the plasma pharmacokinetics of paclitaxel. The present study was therefore conducted to determine whether IRL1620, a selective $ET_B$ receptor agonist, alters the pharmacokinetics of paclitaxel in breast tumor bearing rats.

Methods

IRL1620 was purchased from Sigma-Aldrich (St. Louis, Mo.). Paclitaxel (6 mg/mL solution) was purchased from Ben Venue Laboratories Inc. (Bedford Ohio). Ketamine and xylazine were purchased from Phoenix Scientific, Inc. (St. Joseph, Mo.). [$^3$H]-paclitaxel (ImCi, 6.4 Ci/mmol, specific activity) was purchased from Moravek Biochemicals (Moravek Biochemicals, Calif.). Urethane was purchased from Sigma Aldrich (Sigma Chemicals, St. Louis, Mo.).

Virgin female Sprague Dawley rats (Harlan Co., Madison, Wis.), 48 days old (120-140 g) were used for this study. Upon arrival, all rats were housed three to a cage, in a room with controlled temperature (23±1° C.), humidity (50±10%) and artificial light (0600-1800 hr). The rats were given food and water ad libitum. The experiments were begun only after the rats have been acclimatized to the environment for at least 4 days.

N-methyl-n-nitrosourea (MNU) was administered at a dose of 50 mg/kg, i.p. and rats were palpated twice weekly. Once tumors reached 75-100 mm$^3$, pharmacokinetic studies were performed.

HPLC-UV studies. Rats were anesthetized with a single i.p. injection of urethane (1.5 mg/kg) (Sigma Chemicals, St. Louis, Mo.). The right femoral region was shaved and cleaned with surgical disinfectant and alcohol. The right femoral artery and vein were exposed and cannulated with sterile PE-50 tubing. The neck was shaved and cleaned with surgical disinfectant and alcohol. A middle incision was made around the neck region and the trachea was intubated and connected to a rodent ventilator (Model 683, Harvard Apparatus Inc., South Natick, Mass.). All surgeries were performed under aseptic conditions. Neosporin antibiotic cream (Pfizer, Morris Plains, N.J.) was applied to the wounds to prevent infection. A 45-minute recovery period was given before drug administration.

Normal and tumor bearing rats were used. Paclitaxel was given i.v. (3 mg/kg) 15 minutes after IRL1620 (3 nmol/kg) or vehicle (saline, 3 mL/kg) administration. Blood was collected before IRL1620 administration to provide baseline values. 0.5 mL of blood was drawn from the rats in heparinized syringes at baseline, 5, 30 min, and 2, 6, and 10 h after paclitaxel administration. The samples were centrifuged and plasma was harvested and stored at −80° C. until analysis.

Plasma samples were analyzed for paclitaxel using a HPLC system. Briefly, plasma was thawed and mixed with 50 μL of the internal standard N-cyclohexyl benzamide (3 mM, lower standard curve and 30 mM, higher standard curve) and 3 mL of ethyl ether (Fisher Scientific, Chicago, Ill.) in a 13×100 glass culture tube. The mixture was shaken using a reciprocal shaker for 5 minutes and then centrifuged for 5 minutes at 3,000 rpm at 4° C. The resulting supernatant was transferred to a 13×100 borosilicate glass culture tube and evaporated under a stream of nitrogen in a heated water bath (37° C.). The residue was reconstituted with 200 μL of mobile phase A (50% deionized water, 50% acetonitrile). A 100 μL (lower standard curve and samples collected after IV administration) aliquot of the reconstituted material was injected into a 4 mm NovaPak 150×3.9 mm C18 column (Waters Associates, Milford, Mass.) preceded by a 4 mm NovaPak 20×3.9 mm C18 precolumn using a Waters 2695 separations module connected to a Waters 2487 absorbance detector set at 227 nm. A linear gradient was started with 100% mobile phase A pumped at a flow rate of 1 mL/min. Mobile phase A was then decreased to 70% from 10 to 11 minutes with mobile phase A maintained at 70% from 11 to 16 min to remove materials slowly eluting from the column before the next injection. Subsequently, mobile phase A was increased to 100% from 16 to 17 minutes and maintained at 100% mobile phase A for three minutes providing a total run time of 20 minutes. Plasma concentrations for paclitaxel were calculated from the ratio of the area of the paclitaxel peak to the area of the N-cyclohexyl benzamide peak using least-squares linear regression and weighting by 1/x. Within day and between days variability measured by a coefficient of variation was <10%. Plasma concentration profiles of normal and tumor bearing rats were compared.

Liquid Scintillation counting studies. Rats were anesthetized with a single i.p. injection of a combination of ketamine (100 mg/kg) and xylazine (2 mg/kg). The neck was shaved and cleaned with surgical disinfectant and alcohol. The right carotid artery was exposed and cannulated with sterile PE-50 tubing. A midline incision was made around the neck region and left carotid artery was cannulated with PE50 tubing for blood sampling. Catheters were tunneled subcutaneously and exteriorized at the base of the neck followed by closure of incisions using surgical staples. Buehler et al., Free Radic Biol Med 37:124 (2004). The open tubing was stoppered with a fishing line. All surgeries were performed under aseptic conditions. Neosporin antibiotic cream (Pfizer, Morris Plains, N.J.) was applied to the wounds to prevent infection. A 45-minute recovery period was given before drug administration.

IRL1620 was administered to tumor bearing animals at a dose of 3 nmol/kg, i.v. [$^3$H]-paclitaxel (160 μCi/kg) was mixed with unlabeled paclitaxel. Paclitaxel was administered i.v. 15 minutes following vehicle or IRL1620 administration.

Plasma was collected before vehicle or IRL1620 administration to provide baseline values. Approximately, 0.2 mL of blood was drawn from the rats in heparinized syringes at baseline, 1, 5, 15, 30 min, 1, 2, 4, 6, 8, 12 and 24 h. The samples were centrifuged and plasma was separated and stored at −80° C. until analysis.

The concentrations of [$^3$H]-paclitaxel in the plasma samples were measured using a Beckman Coulter liquid scintillation counter (model LS 6500). Briefly, plasma was thawed and mixed with 20 mL of liquid scintillation cocktail. The samples were counted and the counts were converted from "dpm" units to "fmol/mL" using the following formula:

$$\text{fmol/mL} = \text{dpm value} \times \text{decay factor} \times 2.2 \times 10^{-12} / 10 \times^{-12} \times \text{volume of sample in mL}$$

After conversion into fmol/mL, the pharmacokinetics of the total paclitaxel was calculated using the ratio of [$^3$H]-paclitaxel to unlabeled paclitaxel. Plasma paclitaxel pharmacokinetic estimates were determined using both non-compartmental and compartmental analyses as implemented in WinNonlin Pro 4.1 (Pharsight Corp, Mt. View, Calif.).

In the noncompartmental analysis, the area under the curve (AUC0-∞) was estimated using the trapezoidal rule to the last measurable concentration (Clast) and extrapolated to infinity by dividing Clast by the negative value of the terminal slope (λ) of the log-linear plasma concentration vs. time curve. The following parameters were also calculated: mean residence time (MRTiv) was calculated as the reciprocal of systemic clearance (CL) was calculated as the ratio of dose to AUC0-∞ and apparent volume distribution was calculated the ratio of CL and λ. Plasma half-life was calculated as the product of 0.693 (natural log 2) and MRTiv.

In the compartmental analyses, a series of non-linear compartmental models were fitted to the plasma concentration vs. time curve data. Specifically, one-compartmental, two-compartmental and three-compartmental models were compared. Uniform and Predicted data based weighting were tested. The final selection of the model was based on diagnostic plots (observed vs. predicted and plot of residuals), Akaike Information Criteria (AIC) and Schwartz Criteria (SC). The model with a lower AIC and SC criteria was considered the final model.

Data was analyzed by a One Way ANOVA followed by Duncan's test for HPLC-UV studies and by t-test for liquid scintillation studies. A $p<0.05$ was considered significant. The main outcome measured in these pharmacological response studies was the difference in concentration of paclitaxel in plasma.

Results

Figure 7:
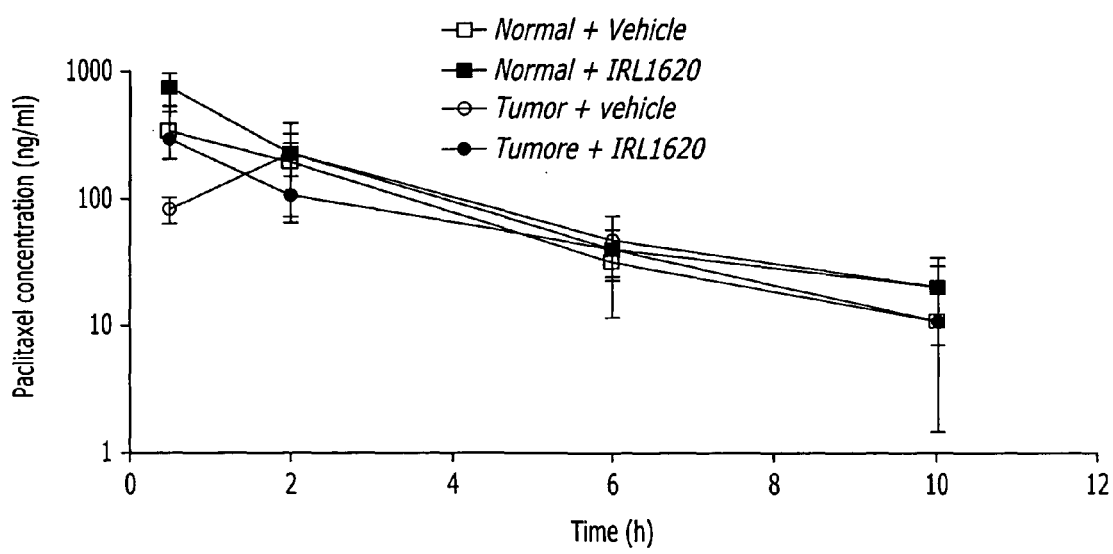
FIG. 7 shows the effect of vehicle or IRL1620 on plasma pharmacokinetics of paclitaxel analysis in normal and tumor bearing rats as determined by HPLC.
Figure 8:
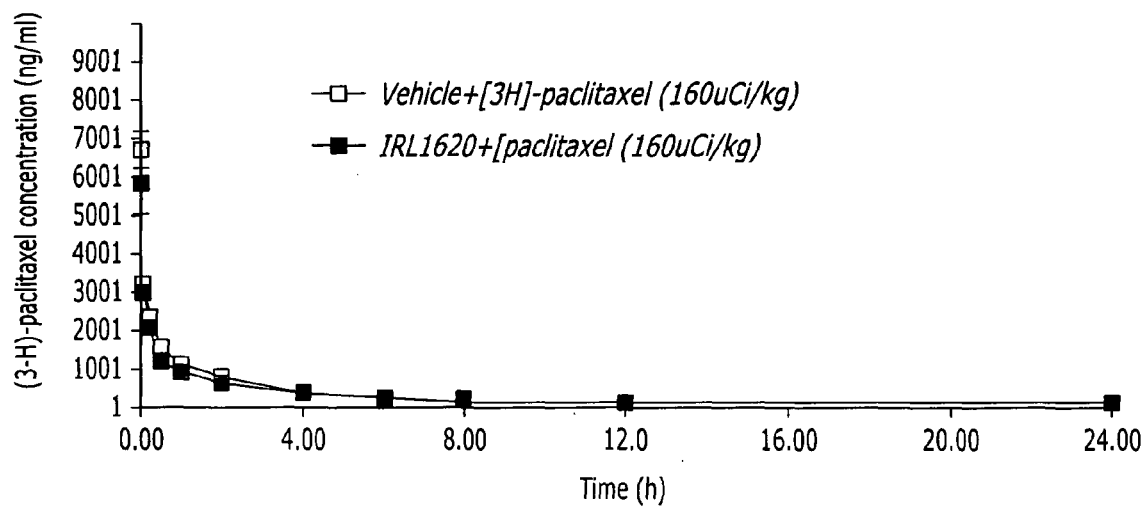
FIGS. 8 and 9 show the effect of vehicle or IRL1620 on plasma pharmacokinetics of [$^3$H]-paclitaxel as determined by liquid scintillation counting.

The pharmacokinetic profile of paclitaxel was not affected by IRL1620 administration (FIGS. 7 and 8) in normal and tumor bearing rats. HPLC analysis of the plasma pharmacokinetic profile is similar to the more extensive profile of radioactive paclitaxel disposition. FIG. 8 depicts the pharmacokinetic profile of paclitaxel radioactivity in vehicle treated and IRL1620 treated tumor bearing rats. The pharmacokinetic profile was analyzed by noncompartmental and compartmental methods.

In the non-compartmental analysis, the AUC calculated for the vehicle+paclitaxel group was 9433.53±1465.00 ng*h/mL and was similar ($p>0.05$) to that of IRL1620 treated tumor rats. The elimination half-life was calculated as 0.14±0.08 hr. The clearance calculated as Dose/AUC was estimated to be 0.56±0.07 L/h/kg. The volume of distribution, calculated as clearance/Kel was found to be 10.11±4.17 L/kg. Overall, and as can be seen in the following table, IRL1620 did not affect the pharmacokinetic profile of paclitaxel.

| Group | Vehicle + Paclitaxel | IRL1620 |
|---|---|---|
| Lambda (h) | 0.14 ± 0.08 | 0.10 ± 0.05 |
| Cmax (μg/mL) | 6.73 ± 0.54 | 5.85 ± 0.77 |
| AUC$_{0-\infty}$ (μg-h/mL) | 9.43 ± 1.47 | 8.63 ± 0.79 |
| Cl (L/h/Kg) | 0.56 ± 0.07 | 0.60 ± 0.06 |
| Vd (L/Kg) | 10.11 ± 4.18 | 9.56 ± 2.90 |

-continued

| Group | Vehicle + Paclitaxel | IRL1620 |
|---|---|---|
| Vss (L/Kg) | 8.14 ± 2.95 | 8.15 ± 2.20 |
| MRT$_{inf}$(h) | 17.43 ± 8.13 | 14.48 ± 4.70 |

Figure 9:
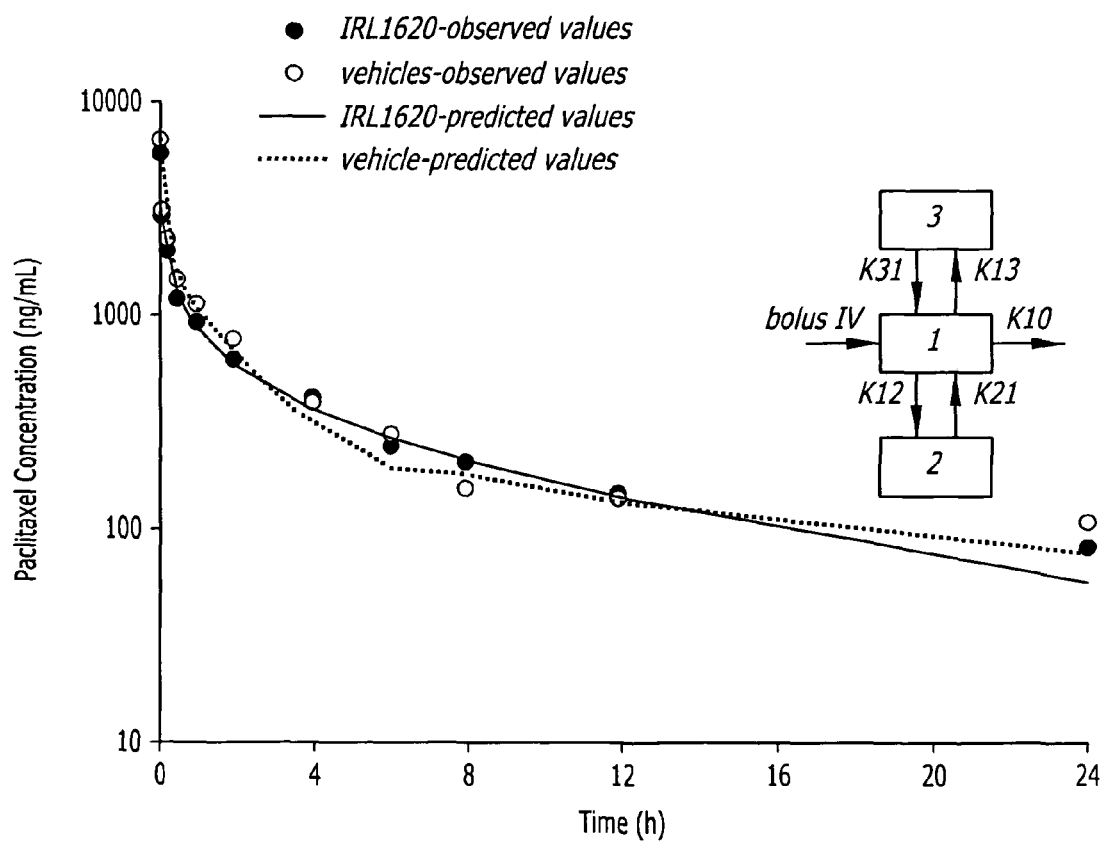

The plasma concentrations of paclitaxel were calculated from the dpm counts in the plasma samples. A three compartmental model best described the pharmacokinetics of paclitaxel. FIG. 9 depicts the observed vs. predicted pharmacokinetic plots for both vehicle treated and IRL1620 treated rats. The AUC of paclitaxel in vehicle treated rats was 9.42±3.18 μg-h/mL. The steady state volume of distribution (Vss) was 10.31±4.54 L/Kg. Clearance was estimated to be 0.69±0.17 L/h/Kg. The α t½, β t½ γ t½ were 0.03±0.01 h, 1.0±0.32 h, and 25.87±17.81 h, respectively. The mean residence time was 27.92±19.84 h. As can be seen in the following table, these parameters estimated in the IRL1620 treated group were not significantly different from that in the vehicle treated group.

| Group | Vehicle + Paclitaxel | IRL1620 |
|---|---|---|
| AUC$_{0-\infty}$ (μg-h/mL) | 9.42 ± 3.18 | 7.25 ± 0.75 |
| Cl (L/h/Kg) | 0.69 ± 0.17 | 0.72 ± 0.09 |
| MRT (h) | 27.92 ± 19.84 | 10.58 ± 3.20 |
| Vss (L/Kg) | 10.31 ± 4.54 | 7.28 ± 1.79 |
| α t$_{1/2}$ | 0.03 ± 0.01 | 0.04 ± 0.01 |
| β t$_{1/2}$ | 1.0 ± 0.32 | 0.84 ± 0.32 |
| γ t$_{1/2}$ | 25.87 ± 17.81 | 9.42 ± 2.59 |
| K$_{10}$ | 3.14 ± 1.34 | 1.72 ± 0.57 |
| K$_{12}$ | 56.47 ± 27.69 | 34.93 ± 23.26 |
| K$_{13}$ | 5.71 ± 3.37 | 3.92 ± 1.88 |

In this study, a three compartmental model best described the plasma pharmacokinetics of paclitaxel. This model suggests that paclitaxel is distributed to various organs whether the blood perfusion in the organs is high, medium or low. IRL1620 administration did not change the distribution of paclitaxel. The plasma pharmacokinetic parameters, generated by the 3-compartment model, displayed comparable clearances, volumes of distribution and absorption, distribution and elimination half-lives for the groups treated with vehicle and IRL1620. However, IRL1620 increases tumor blood perfusion and tumor paclitaxel concentration. Rai et al., American Association of Pharmaceutical Scientists, Pharmaceutics and Drug Delivery Conference. Philadelphia, Pa. (2004); Rai & Gulati, Cancer Chemother Pharmacol, 51:21 (2003). Therefore, IRL1620 selectively increases tumor perfusion without significantly altering the pharmacokinetic profile of paclitaxel.

The use of IRL1620 did not affect the pharmacokinetics of paclitaxel. Often pharmacokinetics can be considered as a surrogate for safety of the compound. Hence these results also suggest that the safety of paclitaxel does not change due to the administration of IRL1620. As a result, IRL1620 could be used to improve paclitaxel efficacy and allow for appropriate dose titration to minimize its severe toxicities. These results show that the pharmacokinetic profile of paclitaxel in normal rats was similar to tumor bearing rats indicating that paclitaxel disposition is not altered by the tumor model system.

EXAMPLE 5

Dose Response Effect of IRL1620, Effect of IRL1620 on the Bio-Distribution of [$^3$H] Paclitaxel in Major Organs and Tumor Tissue and Effect of IRL1620 on Efficacy of Paclitaxel on Tumor Status The experiments described in the present example were designed to determine (a) the dose response effect of $ET_B$ receptor agonist, IRL1620, on breast perfusion of normal and tumor bearing rats, (b) the effect of IRL1620 on the bio-distribution of [$^3$H] paclitaxel in major organs and tumor tissue and (3) the effect of IRL1620 on the efficacy of paclitaxel on tumor status in MNU-induced breast tumor bearing rats.

Methods

IRL1620 was obtained from Sigma Chemical Co. (St. Louis, MO). [$^3$H] paclitaxel was purchased from Moravek Biochemicals (Brea, Calif.). Paclitaxel (6 mg/ml solution) was purchased from Ben Venue Laboratories Inc. (Bedford, Ohio). Ketamine and xylazine were purchased from Phoenix Scientific, Inc. (St. Joseph, Mo.). Tissue solubilizer (TS-2) was purchased from RPI Corp. (Chicago, Ill.).

Virgin female Sprague Dawley rats (Harlan Company, Madison, Wis.) were purchased at 40 days of age and housed two per cage in a temperature-controlled room at 23≅1° C. and maintained under a schedule of 12 h light/12 h dark. They received water and standard rodent diet ad libitum. At 48 days of age, each animal received a single injection of N-methyl nitrosourea (MNU, Ash Stevens, Detroit, Mich.) at a dose of 50 mg/kg. MNU was dissolved in 3% acetic acid and diluted in 0.9% NaCl (final concentration 12.5 mg/ml), was administered by i.p. injection within 30 min of preparation. This treatment induces nearly 100% incidence of mammary adenocarcinoma in rats at approximately 100 days after carcinogen treatment. Mehta Eur J Cancer, 36:1275 (2000). Tumor appearance and location was monitored by manual mammary gland palpation and the tumor surface was measured with a digital caliper. Rats with tumor volume of 500-800 mm$^3$ were selected for the study.

Perfusion study. Perfusion to the rat mammary tissue and tumor was measured using a Periflux PF2b 4000 Laser Doppler Flowmetry (Perimed, Stockholm, Sweden) as previously described. Briefly, rats were anesthetized using ketamine (100 mg/kg) and xylazine (2 mg/kg) as a combined single i.p injection. The fur was shaved around the nipples and the animals were placed on a heating pad (37° C.) to minimize temperature variations. The skin surrounding the mammary glands was dissected out about 6 mm wide and about 4 mm long. A standard model fiber optic probe (MP3 flow probe, Moors Instruments, Devon, England) was applied to the surface of the exposed tissue. It was then connected to a Periflux PF2b 4000 Laser Doppler Flowmetry. The time constant was set to 1.5 s and the bandwidth was set to 4 kHz. This method measures a Doppler shift in the laser light (flux), which is determined by erythrocyte number and velocity, and is proportional to the total blood flow with in a given volume of tissue. Flux values were acquired using Polyview software. A 15 minute baseline of stable recording was obtained before the administration of saline or IRL1620. Animals were administered with 1, 3 or 9 nmol/kg of IRL1620 and the perfusion was recorded for 3 hours. Each dose was administered to at least 4 animals.

Bio-distribution study. Rats were anesthetized with ketamine (100 mg/kg) and xylazine (2 mg/kg) as a combined single i.p injection. Body weight, tumor location and tumor volume of the rats were documented. The animals were randomly grouped to receive saline or IRL1620 (3 nmol/kg) via the tail vain in a final volume of 0.2 ml. Rats from each group received [$^3$H] paclitaxel (40 µCi/rat in 50:50 of Cremophor EL and ethanol) in a final volume of 1.0 ml at 15, 120 and 240 min after IRL1620. Six rats were studied for each time point and total of 36 rats were used. Animals were sacrificed 3 h after the administration of [$^3$H] paclitaxel. The concentration of [$^3$H] paclitaxel was determined in the tumor tissue, kidneys, liver, lung and spleen. The tumor and organs were sliced in to small pieces. About 500 mg of the tissue or tumor were placed in separate vials containing tissue solubilizer (6 ml) and incubated in a water bath at 50° C. The vials were removed from the water bath after the tissue or tumor was dissolved and 1.2 ml of 10% glacial acetic acid was added. The contents of the vial were equally divided into 3 vials and 15 ml of liquid scintillation cocktail (Safety Solve, RPI Corp, Chicago, Ill.) was added to each vial and kept overnight for equilibration. The radioactivity in the tubes was counted using a liquid scintillation counter (Beckman Coulter, LS 6500).

Efficacy study. Tumor bearing animals were randomly divided into seven groups (12 rats/group). Group I—Saline; Group II—IRL1620 (3 nmol/kg); Group III—Cremophor EL:ethanol; Group IV—Vehicle (saline)+paclitaxel (1 mg/kg); Group V—Vehicle (saline)+paclitaxel (5 mg/kg); Group VI—IRL1620 (3 nmol/kg)+paclitaxel (1 mg/kg); and Group VII—IRL1620 (3 nmol/kg)+paclitaxel (5 mg/kg). The dosing schedule was once every three days for a total of 5 doses. Body weight, tumor size and location were monitored on every third day for a total of 30 days after the final dose. The following categories were used for the scoring. Progression: the tumor grows more than 40% in area compared to commencement of treatment; Stasis: the tumor did not fluctuate more than 40% from its initial area throughout the course of treatment; Partial regression: the tumor regressed more than 40% from its initial area; Complete remission: where the tumor is no longer palpable and measurable: Tumor multiplicity (appearance of new tumors) during the treatment and 30 day observation period was also recorded. The animals were sacrificed 30 days after the final (5th) dose. Data were analyzed using analysis of variance followed by Duncan's test. A level of $P<0.05$ was considered significant.

Results

Figure 10A:
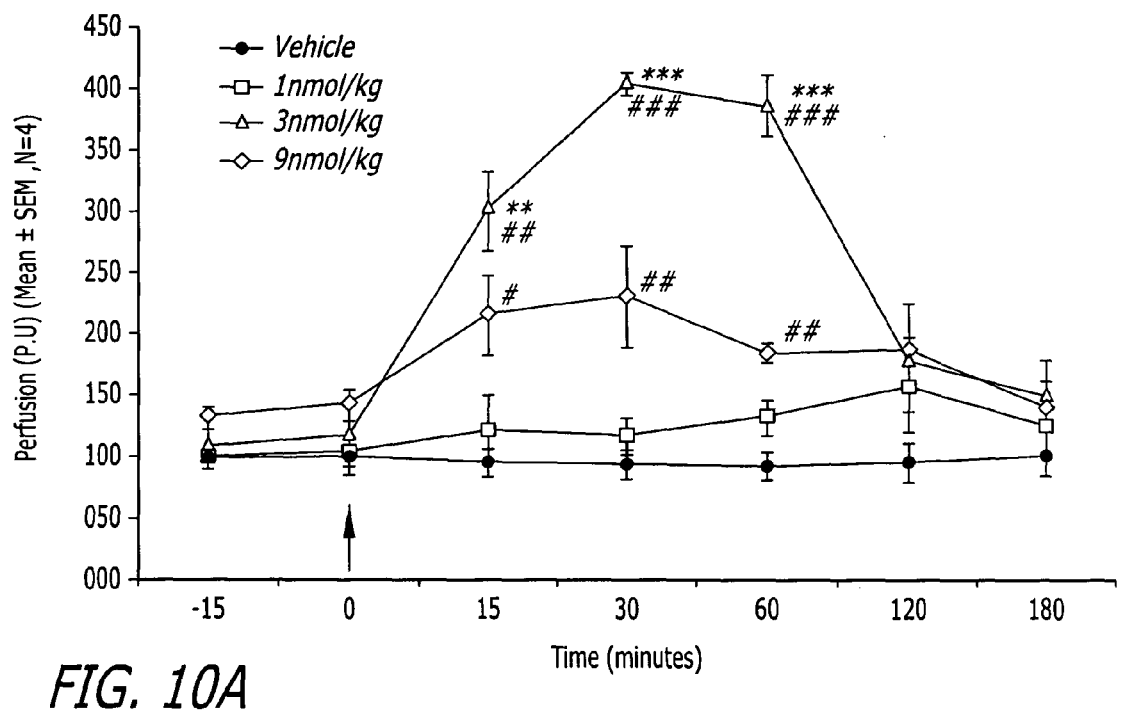
FIGS. 10A and 10B show the effect of IRL1620 on breast tumor perfusion as measured by Laser Doppler Flowmetry.
Figure 10B:
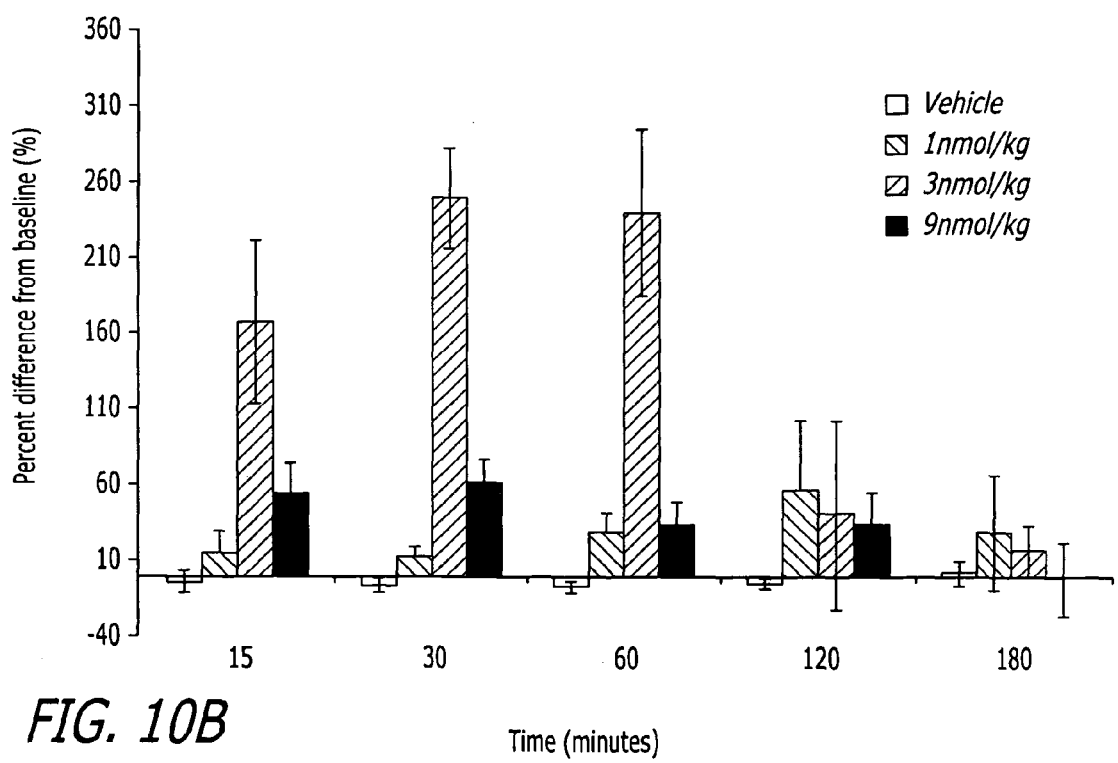

Dose response of IRL1620 on breast perfusion. The effect of IRL1620 administration on tumor perfusion was found to be transient and dose related (FIG. 10A). A maximum increase of 244.0% ($p<0.001$) from the baseline in tumor perfusion was observed at 15 min after the administration of 3 nmol/kg of IRL1620. The increase in perfusion was found to be significant at 15, 30 and 60 minutes compared to baseline as well as saline treated rats. (FIG. 10B). Administration of 1 and 9 nmol/kg of IRL1620 produce only marginal increases in breast tumor perfusion compared to the baseline perfusion and that of saline treated rats. Maximum increases in perfusion (60.9 and 63.3%) were recorded at 90 and 30 min after 1 and 9 nmol/kg of IRL1620, respectively. However, increase in perfusion in animals treated with 9 nmol/kg of IRL1620 was found to be significant at 15, 30 and 60 minutes as compared to saline treated rats (FIG. 1A). Administration of saline to tumor bearing rats did not produce any significant change in blood perfusion compared to baseline (FIG. 10A). Administration of saline, 1, 3 or 9 nmol/kg of IRL1620 did not produce any significant change in breast perfusion in normal female rats (data not shown).

Figure 11:
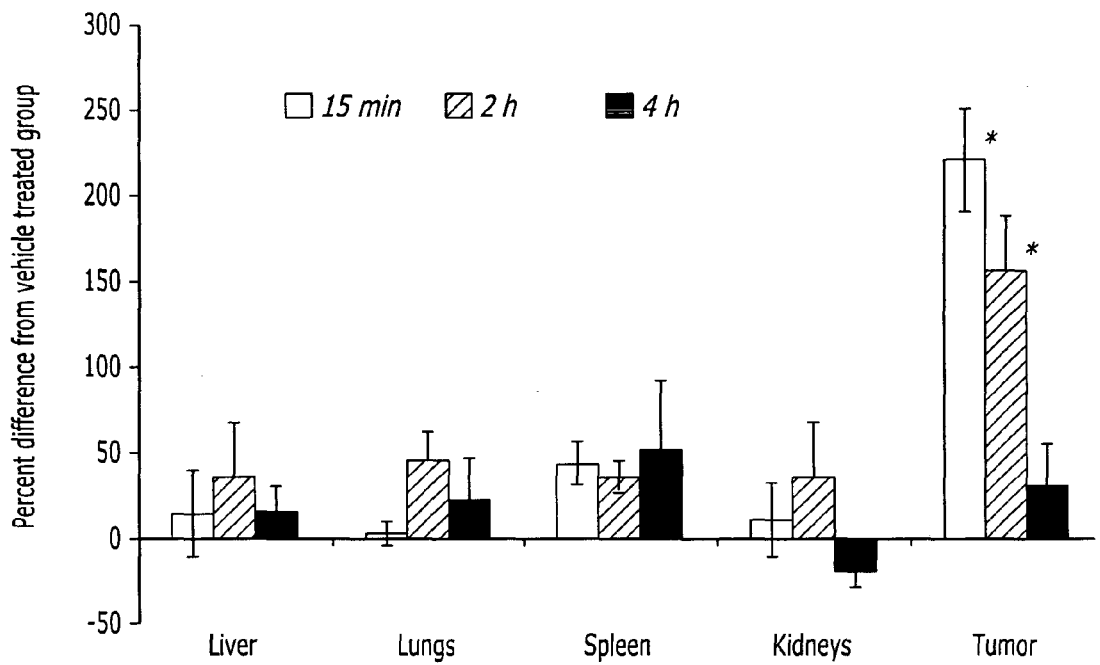
FIG. 11 shows the time dependent effect of IRL1620 administration on [$^3$H] paclitaxel concentration in tumor and major organs of breast tumor bearing rats.

Bio-distribution study. The concentration of [$^3$H] paclitaxel in the tumor was significantly increased in IRL1620 (3 nmol/kg) treated rats compared to saline treated rats. The maximal effect was noticed in the group of animals administered paclitaxel 15 min after IRL1620. An increase of 277.1, 151:9 and 34.7% in tumor paclitaxel concentration was observed when paclitaxel was administered 15, 120 and 240 min, respectively after IRL1620 administration (FIG. 11). It was found that IRL1620 administration did not alter the accumulation of paclitaxel in the liver, lungs, kidneys and spleen compared to control animals (FIG. 11).

Figure 12:
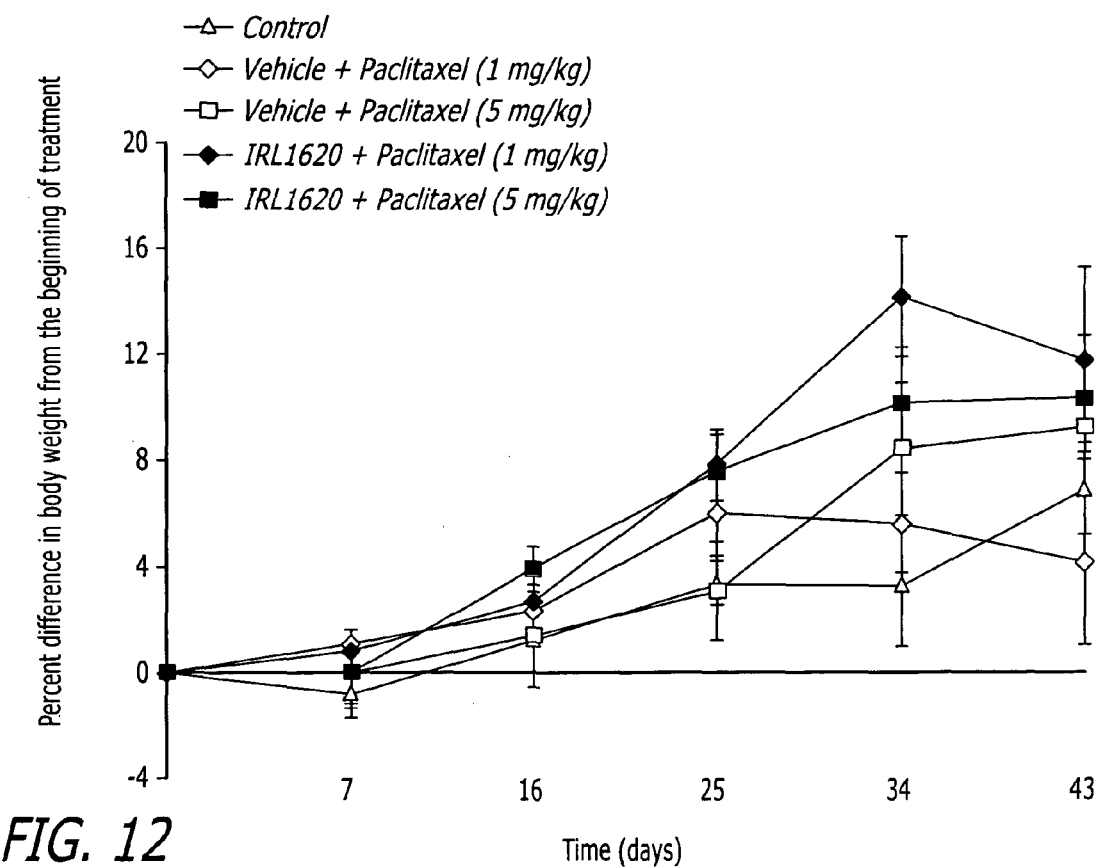
FIG. 12 shows the percentage difference in the body weight of breast tumor bearing rats compared to the beginning of treatment.

Efficacy study: Body weight. The percentage differences in body weight of animals from baseline (before starting treatment) to 30 days after final dose are given in FIG. 12. The percentage increase in body weight as monitored at the end of the experiment in saline treated control rats were 7.2±1.7% compared to baseline body weight (FIG.12). There was a 5.1±3.6, 9.4±2.4, 14.3±3.1 and 13.1±1.8% increase in body weight in the group of animals treated with vehicle+paclitaxel (1 mg/kg), vehicle+paclitaxel (5 mg/kg), IRL1620+paclitaxel 1 mg/kg and IRL1620+paclitaxel 5 mg/kg, respectively (FIG. 12). The percentage increase in body weight of animals administered with Cremophor EL:ethanol and IRL1620 compared to baseline was found to be <10% (data not shown).

Figure 13:
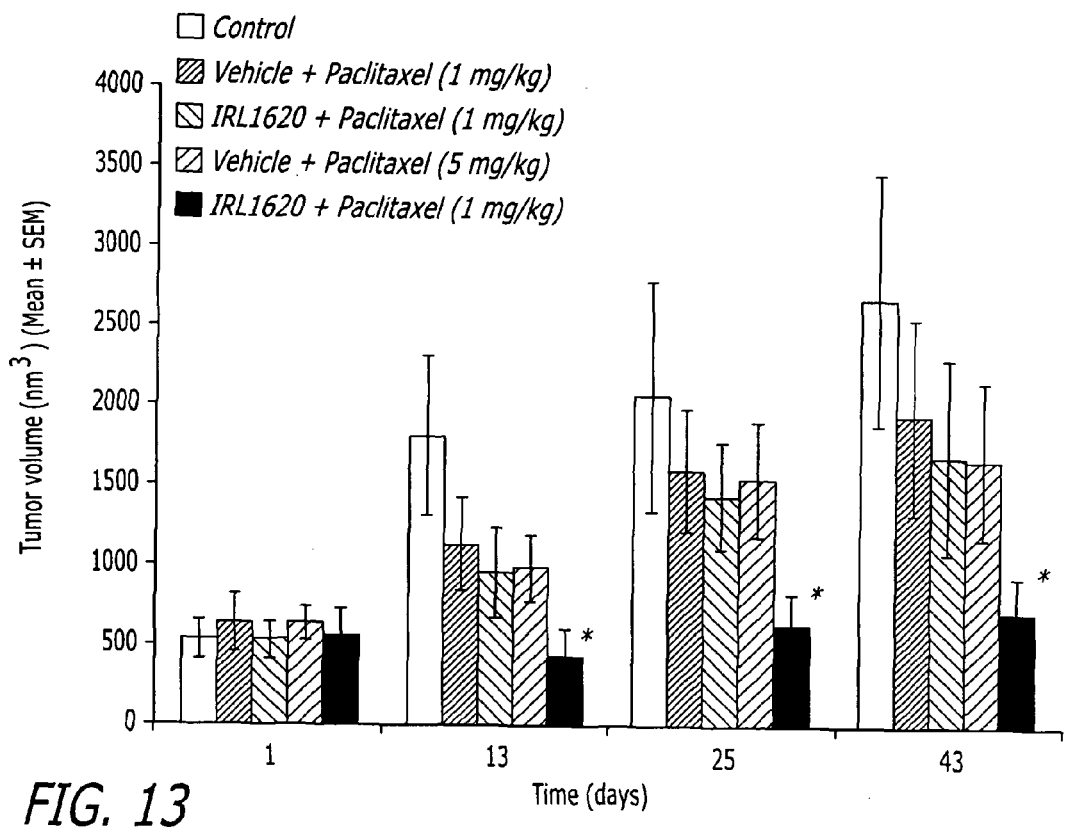
FIG. 13 shows the effect of IRL1620 administration on the tumor volume of breast tumor bearing rats.

Efficacy study: Tumor volume. Tumor sizes in various groups were comparable and not significantly different from each other at the commencement of treatment (FIG. 13). The tumor volume of control rats increased at a rapid and variable rate. Large variability in tumor growth may be attributed to the random growth pattern of autochthonously growing tumors. At the end of the 30 day observation period, the control tumors had a tumor volume of 2693.4±790.9 mm$^3$. IRL1620 treated rats had a similar pattern of development with a final tumor volume of 2560.5±844.4 mm$^3$. Cremophor EL:Ethanol treatment also resulted in a similar growth pattern with a final tumor volume of 2338±1329 mm$^3$. Thus, IRL1620 and cremophor El:ethanol did not have a significant effect on the growth of MNU-induced breast tumors. Vehicle+paclitaxel 1 mg/kg treated rats showed a slightly reduced growth in tumor size (1960.8±611.9 mm$^3$) which was more pronounced in the vehicle+paclitaxel 5 mg/kg group (1682.7±497.3 mm$^3$) when compared to control rats. IRL1620+paclitaxel 1 mg/kg treated rats showed reduced tumor size (1707.2±621.1 mm$^3$). However, the lowest average tumor size (730.1±219.4 mm$^3$) was observed in the group of animals treated with IRL1620+paclitaxel 5 mg/kg (FIG. 13). IRL1620 followed by paclitaxel 5 mg/kg on every third day for a total of 5 doses significantly (p<0.05) reduced the tumor volume compared to saline+paclitaxel (5 mg/kg) administered rats (FIG. 13). Tumor volume was also found to be lower in IRL1620+paclitaxel 5 mg/kg group compared to rats treated with either IRL1620 or cremophor EL:ethanol (data not shown).

Efficacy study: Tumor multiplicity. Animals in all treatment groups developed additional tumors by the end of 30 day observation period. There was a 58.4, 57.1 and 60.8% increase in additional tumor appearance in animals treated with saline, cremophor EL:ethanol and IRL1620, respectively. New tumor occurrence was found to be 78.3 and 41% in animals administered with vehicle+paclitaxel 1 and 5 mg/kg, respectively. However, percent of additional tumors was found to be 69.2 and 44.8% in IRL1620+paclitaxel 1 and 5 mg/kg, respectively.

Figure 14:
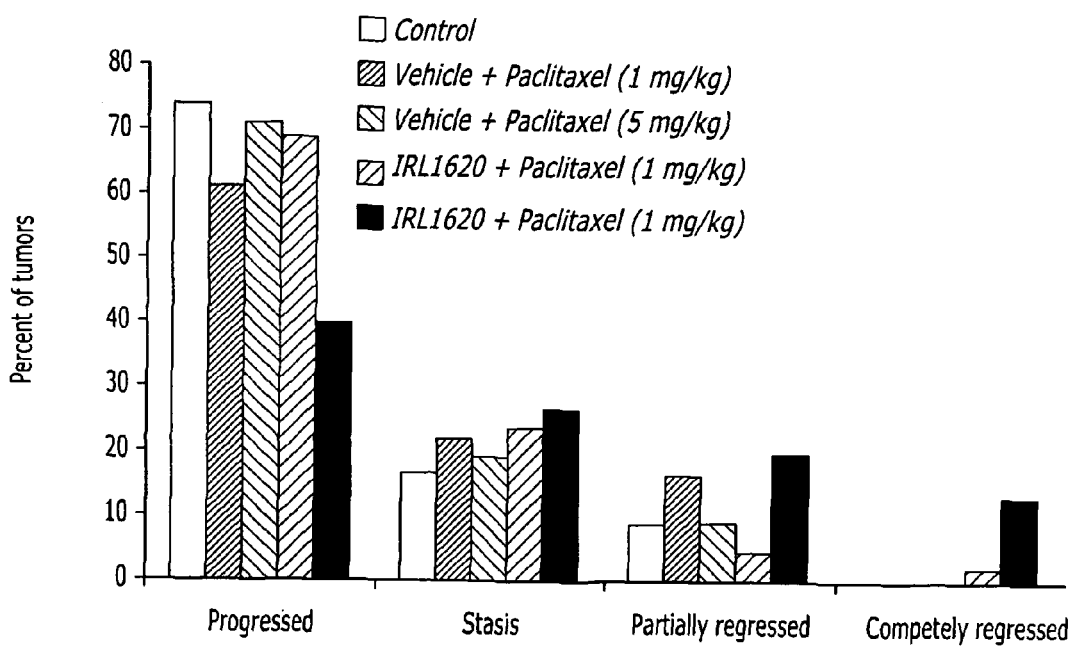
FIG. 14 shows the effect of IRL1620 administration on tumor progression, stasis and regression.

Efficacy study: Tumor progression. The percent of tumors that progressed, remained in stasis, regressed or disappeared were calculated as described previously. 73.5% of tumors in the saline treated group progressed above 40% of the initial tumor size. IRL1620 (82.7%) and cremophor EL:ethanol (80.4%) treated groups had similar percent of tumors progressing past 40% of the initial tumor size. A lower percent of tumors had progressed in the vehicle+paclitaxel (5 mg/kg) group (71.4%), vehicle+paclitaxel (1 mg/kg) group (61.1%) and IRL1620+paclitaxel (1 mg/kg) groups (69%). But, the lowest percent (40%) was seen in the IRL1620+paclitaxel (5 mg/kg) group (FIG. 14).

Efficacy study: Tumor stasis. 16.9% of the tumors in the saline treated rats remained in stasis, not growing beyond the 40% range by the 30-day end point. IRL1620 (13.7%), cremophor EL: ethanol (15.2%), vehicle+paclitaxel (1 mg/kg) (22.2%) and vehicle+paclitaxel (5 mg/kg) (19.5%) treated rats showed a lower percent of tumors that remained in stasis. IRL1620+paclitaxel (1 mg/kg) (23.8%) treated rats and IRL1620+paclitaxel (5 mg/kg) treated rats showed the greatest percent of tumors that remained in stasis (26.6%) (FIG. 14).

Efficacy study: Tumor regression. Administration of IRL1620 prior to paclitaxel 5 mg/kg treatment significantly reduced the progression of tumors compared to control animals. The saline treated rats showed a 9.2% of tumors regressing from the initial tumor volume. Cremophor EL:ethanol (4.3%), IRL1620 (3.4%) and vehicle+paclitaxel (5 mg/kg) (9.5%) treated rats were not significantly different from the control group in the percent of tumors regressing in size. At the end of 5th dose, tumors had regressed by 76.1±10.5 and 45.9±11.5% in the IRL1620+paclitaxel 5 mg/kg treated rats and vehicle+paclitaxel 5 mg/kg treated rats, respectively compared to control rats. There was a 80.2±6.9% (p<0.05) and 33.8±19.4% regression in animals treated with IRL1620+paclitaxel 5 mg/kg and vehicle+paclitaxel 5 mg/kg group, respectively (FIG. 14). The tumor regression rate in IRL1620+paclitaxel 1 mg/kg and vehicle+paclitaxel (1 mg/kg) group was found to be 47.1±15.4 and 37.7±16.2%, respectively. Administration of paclitaxel (5 mg/kg) 15 min after IRL1620 produced significantly greater tumor regression compared to administration of paclitaxel (5 mg/kg) 15 min after saline. The cremophor El:ethanol and IRL1620 treated groups were not significantly different in their tumor regression compared to the control rats at any point of time (data not shown).

Efficacy study: Tumor remission. Complete regression, where the tumors completely disappeared, was only observed in two groups. IRL1620+paclitaxel (1 mg/kg) (2.3%) and IRL1620+paclitaxel (5 mg/kg) (15%) treated rats (FIG. 14).

The results obtained in the present study show that administration of 3 nmol/kg dose IRL1620 produces a significant increase in tumor perfusion compared to baseline and vehicle treated rats. Although 1, 3 and 9 nmol/kg of IRL1620 increase tumor perfusion, 3 nmol/kg dose of IRL1620 produced maximal effect. It is possible that the higher dose (9 nmol/kg) also stimulates $ET_B$ receptors that are responsible for vasoconstriction. Brooks et al., J Cardiovasc Pharmacol, 26 Suppl 3:S322 (1995).

Therefore, vasodilatation combined with vasoconstriction due to $ET_B$ receptor stimulation at high dose leads to a reduced vasodilator effect. The lower dose (1 nmol/kg) may not be enough to produce maximal vasodilatation. Hence, the 3 nmol/kg dose of IRL1620 was selected for subsequent studies.

The effect of IRL1620 on paclitaxel concentration in tumor tissue was found to be time dependent. There was a 277.1, 151.9 and 34.7% difference in tumor [$^3$H] paclitaxel concentration when [$^3$H] paclitaxel was administered 15 min, 2 h and 4 h, respectively after IRL1620 administration compared to vehicle treated rats. Studies showed that IRL1620 administration did not lead to significant increase in the accumulation of paclitaxel in the liver, lungs, kidneys and spleen. Results of the efficacy study indicate that administration of IRL1620 significantly increased paclitaxel induced reduction in tumor volume compared to saline treated rats administered with paclitaxel. The enhanced therapeutic benefit seen in the 5 mg/kg dose of paclitaxel was maintained till 30 days after the final dose. This indicates that there was no relapse of the tumor volume and the effect of IRL1620 in enhancing the efficacy of paclitaxel remained consistent till the end of the study. However, saline treatment followed by paclitaxel (1 and 5 mg/kg) did not produce such a significant change in tumor growth. Additionally, tumor multiplicity was reduced in the group of rats treated with IRL1620 followed by paclitaxel 5 mg/kg. Thus, IRL1620 administration prior to paclitaxel 5 mg/kg has a significant effect on paclitaxel efficacy. This is illustrated by the decrease in tumor burden, percent of tumor regression, unaffected body weight and multiplicity. Further, there was a 2.3 and 15% complete remission of the initial tumors in the group of animals treated with IRL1620 followed by paclitaxel 1 and 5 mg/kg, respectively compared to any other group.

The experiments described in this example clearly show that the $ET_B$ receptor agonist, IRL1620 could significantly increase tumor blood flow. Administration of IRL1620 produced an increase in tumor blood flow, whereas the perfusion in control healthy tissue was not altered. The increase in tumor perfusion lasted for 3 hours. Administration of [$^3$H] paclitaxel during the window of elevated perfusion significantly increased the concentration of [$^3$H] paclitaxel in the tumor tissue only but not in other organs. Moreover, the results of the experiments described in this example provide evidence that administration of IRL1620 could galvanize the anti-tumor efficacy of paclitaxel. There was a 60.0% reduction in tumor volume of rats treated with paclitaxel 5 mg/kg, every third day for a total of 5 doses, as compared to control rats. However, paclitaxel administration 15 minutes after IRL1620 administration reduced the tumor volume to 268.9% compared to control rats when recorded one month after the last dose of paclitaxel. There was a 130.4% reduction in tumor volume in rats administered IRL1620 as compared to paclitaxel alone treated rats. There is a possibility that the elevated tumor perfusion may increase the availability of nutrients that might facilitate tumor growth. Our results show that there was no significant increase in tumor volume and tumor multiplicity of IRL1620 treated rats compared to saline treated rats, indicating that IRL1620 alone did not produce any effect on tumor volume and multiplicity. In conclusion, IRL1620 can be used as a tumor-selective vasodilator and can be used to selectively increase the efficacy of chemotherapy. The present study clearly demonstrates that multi-fold higher drug concentrations can be achieved in the tumor tissue by adopting this therapeutic strategy. Finally, $ET_A$ receptor antagonists have also been proposed to improve tumor blood flow (Sonveaux et al., Cancer Res, 64:3209 (2004)) and can be used to enhance delivery of anticancer drugs to the tumor in accordance with the present invention.

Pharmaceutical compositions containing the active ingredients are suitable for administration to humans or other mammals. Typically, the pharmaceutical compositions are sterile, and contain no toxic, carcinogenic, or mutagenic compounds that would cause an adverse reaction when administered. Administration of the pharmaceutical composition can be performed before, during, or after the onset of solid tumor growth.

A method of the present invention can be accomplished using active ingredients as described above, or as a physiologically acceptable salt, derivative, prodrug, or solvate thereof. The active ingredients can be administered as the neat compound, or as a pharmaceutical composition containing either or both entities.

The pharmaceutical compositions include those wherein the active ingredients are administered in an effective amount to achieve their intended purpose. More specifically, a "therapeutically effective amount" means an amount effective to prevent development of, to eliminate, to retard the progression of, or to reduce the size of a solid tumor. Determination of a therapeutically effective amount is well within the capability of those skilled in the art, especially in light of the detailed disclosure provided herein.

A "therapeutically effective dose" refers to that amount of the active ingredients that results in achieving the desired effect. Toxicity and therapeutic efficacy of such active ingredients can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the active ingredients preferably lies within a range of circulating concentrations that include the $ED_{50}$ with little or no toxicity. The dosage can vary within this range depending upon the dosage form employed, and the route of administration utilized.

The exact formulation and dosage is determined by an individual physician in view of the patient's condition. Dosage amount and interval can be adjusted individually to provide levels of the active ingredients that are sufficient to maintain therapeutic or prophylactic effects.

The amount of pharmaceutical composition administered can be dependent on the subject being treated, on the subject's weight, the severity of the affliction, the manner of administration, and the judgment of the prescribing physician.

The active ingredients can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active ingredients into preparations which can be used pharmaceutically.

When a therapeutically effective amount of the active ingredients is administered, the composition can be in the form of a pyrogen-free, parenterally acceptable aqueous solution. The preparation of such parenterally acceptable solutions, having due regard to pH, isotonicity, stability, and the like, is within the skill in the art. A preferred composition for intravenous injection typically will contain an isotonic vehicle although this characteristic is not required.

For veterinary use, the active ingredients are administered as a suitably acceptable formulation in accordance with normal veterinary practice. The veterinarian can readily determine the dosing regimen that is most appropriate for a particular animal.

Various adaptations and modifications of the embodiments can be made and used without departing from the scope and spirit of the present invention which can be practiced other than as specifically described herein. The above description is intended to be illustrative, and not restrictive. The scope of the present invention is to be determined only by the claims.

The terms and expressions which have been employed herein are used as terms of description and not of limitation, and there is no intention in the use of such terms and expressions of excluding equivalents of the features shown and described, or portions thereof, it being recognized that various modifications are possible within the scope of the present invention claimed. Moreover, any one or more features of any embodiment of the present invention can be combined with any one or more other features of any other embodiment of the present invention, without departing from the scope of the present invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the present invention otherwise claimed. No language in the specification should be construed as indicating any non-claimed element essential to the practice of the present invention.

Groupings of alternative elements or embodiments of the present invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A method of selectively increasing delivery of a chemotherapeutic agent to a breast tumor comprising intravenously administering to a mammal in need thereof IRL-1620 and said chemotherapeutic agent, wherein said IRL-1620 selectively increases blood flow to said breast tumor, thereby increasing the delivery of said chemotherapeutic agent to said breast tumor, further wherein said IRL-1620 is administered before said chemotherapeutic agent.

2. The method according to claim 1, wherein the pharmacokinetics of said chemotherapeutic agent are not affected by said IRL-1620.

3. The method according to claim 1, wherein said IRL-1620 enhances the efficacy of said chemotherapeutic agent.

4. The method according to claim 1, wherein said chemotherapeutic agent is selected from the group consisting of adriamycin, camptothecin, carboplatin, cisplatin, daunorubicin, doxorubicin, alpha interferon, beta interferon, gamma interferon, interleukin 2, irinotecan, docetaxel, paclitaxel, topotecan, and mixtures thereof.

5. The method according to claim 4, wherein said chemotherapeutic agent is paclitaxel.

6. The method according to claim 1, wherein said mammal is a human.

7. The method according to claim 1, wherein said IRL-1620 is administered at least 15 minutes before said chemotherapeutic agent.

8. The method according to claim 1, wherein said IRL-1620 is administered 15 minutes to 240 minutes before said chemotherapeutic agent.

9. The method according to claim 1, wherein said IRL 1620 is administered 15 minutes to 180 minutes before said chemotherapeutic agent.

10. The method according to claim 1, wherein said IRL 1620 is administered 15 minutes to 120 minutes before said chemotherapeutic agent.

11. The method according to claim 1, wherein said IRL 1620 is administered 15 minutes to 60 minutes before said chemotherapeutic agent.

12. The method according to claim 1, wherein said IRL 1620 is administered 15 minutes to 30 minutes before said chemotherapeutic agent.

* * * * *